US012731007B2

(12) United States Patent
Dahlem et al.

(10) Patent No.: US 12,731,007 B2
(45) Date of Patent: Sep. 8, 2026

(54) TEMPORAL SEQUENCE CAUSAL TRANSFORMER MACHINE LEARNING MODEL

(71) Applicant: UnitedHealth Group Incorporated, Minnetonka, MN (US)

(72) Inventors: Dominik Roman Christian Dahlem, Dublin (IE); Vijay S. Nori, Roswell, GA (US); Eran Halperin, Santa Monica, CA (US); Nadav Rakocz, Los Angeles, CA (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 622 days.

(21) Appl. No.: 18/331,600

(22) Filed: Jun. 8, 2023

(65) Prior Publication Data

US 2024/0169264 A1 May 23, 2024

Related U.S. Application Data

(60) Provisional application No. 63/384,941, filed on Nov. 23, 2022.

(51) Int. Cl.

| | |
|---|---|
| ***G06N 3/0455*** | (2023.01) |
| ***G06N 3/047*** | (2023.01) |
| ***G06N 3/092*** | (2023.01) |
| ***G06N 20/00*** | (2019.01) |
| ***G16H 10/60*** | (2018.01) |

(52) U.S. Cl.

CPC .......... *G06N 3/0455* (2023.01); *G06N 3/047* (2023.01); *G06N 3/092* (2023.01); *G06N 20/00* (2019.01); *G16H 10/60* (2018.01)

(58) Field of Classification Search

CPC ...... G06N 3/0455; G06N 3/047; G06N 3/092; G06N 20/00; G16H 10/60

See application file for complete search history.

(56) References Cited

U.S. PATENT DOCUMENTS

| | | | |
|---|---|---|---|
| 5,550,734 | A | 8/1996 | Tarter et al. |
| 6,073,104 | A | 6/2000 | Field |
| 8,370,172 | B2 | 2/2013 | Shell et al. |
| 9,697,469 | B2 | 7/2017 | Mcmahon et al. |

(Continued)

OTHER PUBLICATIONS

Chen, X., Yao, L., McAuley, J., Zhou, G., & Wang, X. (2021). A survey of deep reinforcement learning in recommender systems: A systematic review and future directions. arXiv preprint arXiv:2109.03540. (Year: 2021) .*

(Continued)

*Primary Examiner* — James T Tsai

(74) *Attorney, Agent, or Firm* — Alston & Bird LLP

(57) ABSTRACT

Various embodiments of the present disclosure provide methods, apparatus, systems, computing devices, computing entities, and/or the like for generating a prediction output comprising one or more actions by receiving data associated with encounters in a tuple form, tokenizing the encounters, training a causal transformer machine learning model configured to predict outcomes of actions by translating action tokens from the tokenized encounters into one or more embedding spaces, and training a causal transformer machine learning model to select the one or more actions based on embeddings from the one or more embedding spaces.

20 Claims, 5 Drawing Sheets

(56) References Cited

U.S. PATENT DOCUMENTS 10,133,250 B2 11/2018 Kohn et al.
10,366,451 B2 7/2019 Kaznady
10,755,816 B2 8/2020 Bennett et al.
10,885,432 B1 * 1/2021 Dulac-Arnold ........ G06N 3/006
11,107,159 B2 8/2021 Hails et al.
11,177,025 B2 11/2021 Bettencourt-Silva et al.
11,295,861 B2 4/2022 Al Hasan et al.
11,490,966 B2 11/2022 Roche et al.
11,600,387 B2 3/2023 Peng et al.
11,615,208 B2 3/2023 Truong et al.
12,334,192 B2 * 6/2025 Singal .................... G16H 50/20
12,626,050 B2 5/2026 Mallinson et al.
2005/0216315 A1 9/2005 Andersson
2007/0073685 A1 3/2007 Thibodeau et al.
2009/0192831 A1 7/2009 Raynes et al.
2012/0324113 A1 12/2012 Prince et al.
2013/0275144 A1 10/2013 Bain
2014/0081652 A1 3/2014 Klindworth
2015/0339769 A1 11/2015 Deoliveira et al.
2017/0024643 A1 * 1/2017 Lillicrap ................ G06N 3/006
2017/0076201 A1 * 3/2017 van Hasselt ............. G06N 3/08
2017/0091861 A1 3/2017 Bianchi et al.
2017/0286622 A1 10/2017 Cox et al.
2018/0260891 A1 9/2018 Merrill et al.
2019/0372644 A1 * 12/2019 Chen ...................... G06N 3/126
2020/0134716 A1 4/2020 Lahrichi et al.
2020/0226690 A1 7/2020 Gulati et al.
2020/0286056 A1 9/2020 Martino et al.
2021/0158085 A1 5/2021 Budzik
2021/0202055 A1 7/2021 Xiao et al.
2021/0295130 A1 * 9/2021 Rasoolinejad ....... G06V 40/176
2021/0319054 A1 10/2021 Glass et al.
2021/0387330 A1 * 12/2021 Mavrin ................. G06N 3/092
2022/0019888 A1 1/2022 Aggarwal et al.
2022/0084664 A1 3/2022 Ginsburg
2022/0374608 A1 11/2022 Shazeer et al.
2022/0398460 A1 12/2022 Dalli et al.
2023/0040705 A1 2/2023 Loganathan et al.
2023/0121711 A1 4/2023 Chhaya et al.
2024/0028907 A1 1/2024 Shi et al.
2024/0104379 A1 * 3/2024 Laskin .................. G06N 3/092

OTHER PUBLICATIONS

Chen, Lilli et al. "Decision Transformer: Reinforcement Learning via Sequence Modeling", Advances in Neural Information Processing Systems, 21 pages, Jun. 24, 2021, https://arxiv.org/abs/2106.01345.

Cortaredona, Sébastien et al. "The Extra Cost of Comorbidity: Multiple Illnesses and the Economic Burden of Non-Communicable Diseases", BMC Medicine, 17 pages, Dec. 8, 2017, https://bmcmedicine.biomedcentral.com/articles/10.1186/s12916-017-0978-2.

Festor, Paul et al. "Assuring the Safety of AI-based Clinical Decision Support Systems: A Case Study of the AI Clinician for Sepsis Treatment," BMJ Health and Care Informatics, 9 pages, Jul. 17, 2022, ISSN 2632-1009. Https://informatics.bmj.com/content/29/1/e100549.

Fringuellotti et al., "Insurance Companies and the Growth of Corporate Loans' Securitization", Federal Reserve Bank of New York, 67 pages, Aug. 2021, http://hdl.handle.net/10419/247898.

Hernan, Miguel A. et al. "Causal Inference", 102 pages, Mar. 19, 2014, ISBN 978-1-315-37493-2.

Hu, Shengchao, et al. "On Transforming Reinforcement Learning by Transformer: The Development Trajectory", arXiv preprint arXiv:2212.14164, 26 pages, Jan. 20, 2023, https://arxiv.org/abs/2212.14164.

Huang, Yong et al., "Reinforcement Learning For Sepsis Treatment: A Continuous Action Space Solution", Machine Learning for Healthcare, 17 pages, Dec. 31, 2022, https://www.mlforhc.org/s/93Reinforcement_learning_for_sepsis-2.pdf.

Humphrey, Kyle, "Using Reinforcement Learning to Personalize Dosing Strategies in a Simulated Cancer Trial with High Dimensional Data", The University of Arizona, 50 pages, (2017), https://repository.arizona.edu/handle/10150/625341.

Imbens, Guido W., "The Role of the Propensity Score in Estimating Dose-Response Functions", Biometrika, vol. 87, No. 3, 22 pages, Sep. 2000, https://www.jstor.org/stable/2673642.

Janner, Michael et al., "Offline Reinforcement Learning as One Big Sequence Modeling Problem", Advances in Neural Information Processing Systems, vol. 4, 17 pages, Nov. 29, 2021, https://arxiv.org/abs/2106.02039.

Komorowski, Matthleu, et al. "The Artificial Intelligence Clinician Learns Optimal Treatment Strategies for Sepsis in Intensive Care", Nature Medicine, vol. 24, 11 pages, (2018), https://doi.org/10.1038/s41591-018-0213-5.

Krajna, Agneza et al., "Explainability in Reinforcement Learning: Perspective and Position," arXiv preprint arXiv:2203.11547, vol. 1, 18 pages, Mar. 22, 2022, https://arxiv.org/pdf/2203.11547.

Liu, Mingyang et al. "Deep Reinforcement Learning for Personalized Treatment Recommendation," Statistics in Medicine, vol. 41, 23 pages, May 22, 2022, https://onlinelibrary.wiley.com/doi/epdf/10.1002/sim.9491.

Michalowski, Martin, et al. "MitPlan 2.0: Enhanced Support for Multi-morbid Patient Management Using Planning", Artificial Intelligence in Medicine, 11 pages, (2021), https://doi.org/10.1007/978-3-030-77211-6_31.

Peng, Xuefeng et al. "Improving Sepsis Treatment Strategies by Combining Deep and Kernel-Based Reinforcement Learning", MIT, Institute for Medical Engineering & Science, 10 pages, Dec. 5, 2018, https://www.ncbi.nlm.nih.gov/pmc/articles/PMC6371300/.

Petropoulos ,Anastasios, et al. "A Robust Machine Learning Approach for Credit Risk Analysis of Large Loan Level Datasets Using Deep Learning and Extreme Gradient Boosting", Irving Fisher Committee On Central Bank Statistics—IFC Bulletins Chapters, 45 pages, Aug. 30, 2018, https://ideas.repec.org/h/bis/bisifc/49-49.html.

Prasad, Niranjani et al. "A Reinforcement Learning Approach to Weaning of Mechanical Ventilation in Intensive Care Units", arXiv preprint arXiv:1704.06300, 10 pages, Apr. 20, 2017, https://arxiv.org/abs/1704.06300.

Raghu, Aniruddh et al. "Deep Reinforcement Learning for Sepsis Treatment", Machine Learning For Health, vol. 1, 9 pages, Nov. 27, 2017, https://arxiv.org/abs/1711.09602.

Rosenbaum, Paul et al. "The Central Role of the Propensity Score in Observational Studies for Causal Effects", Biometrika, vol. 70, Issue 1, pp. 41-55, Apr. 1, 1983, https://academic.oup.com/biomet/article/70/1//41/240879.

Tang, Shengpu, et al. "Leveraging Factored Action Spaces for Efficient Offline Reinforcement Learning in Healthcare," Advances in Neural Information Processing Systems, vol. 35, 15 pages, (2022), https://papers.nips.cc/paper_files/paper/2022/hash/dda7f9378a210c25e470e19304cce85d-Abstract-Conference.html.

Tseng, Huan-Hsin et al. "Deep Reinforcement Learning for Automated Radiation Adaptation in Lung Cancer," American Association of Physicists in Medicine, vol. 44, 16 pages, Dec. 2017, ISSN 2473-4209. doi: 10.1002/mp.12625.

Watts, Jeremy, et al. "Optimizing Individualized Treatment Planning for Parkinson's Disease Using Deep Reinforcement Learning", 42nd Annual International Conference of the IEEE Engineering in Medicine & Biology Society, 4 pages, (2020), doi: 10.1109/EMBC44109.2020.9175311.

Wennberg, John E., et al. "Unwarranted Variations in Healthcare Delivery: Implications for Academic Medical Centres", National Library of Medicine, vol. 325, 4 pages, Oct. 26, 2002, https://www.ncbi.nlm.nih.gov/pmc/articles/PMC1124450/.

Yauney, Gregory, et al. "Reinforcement Learning with Action-Derived Rewards for Chemotherapy and Clinical Trial Dosing Regimen Selection", Machine Learning for Healthcare, 65 pages, (2018), https://proceedings.mlr.press/v85/yauney18a/yauney18a.pdf.

Zhao, Siyan, et al. "Decision Stacks: Flexible Reinforcement Learning via Modular Generative Models", NeurIPS, 18 pages, Oct. 29, 2023, https://arxiv.org/abs/2306.06253.

(56) References Cited

OTHER PUBLICATIONS

Zhao, Yufan, et al. "Reinforcement Learning Strategies for Clinical Trials in Nonsmall Cell Lung Cancer", Biometrics, vol. 67, 22 pages, Dec. 2011, https://www.ncbi.nlm.nih.gov/pmc/articles/PMC3138840/.
Ho Oh, et al., "Reinforcement Learning-Based Expanded Personalized Diabetes Treatment Recommendation Using South Korea Electronic Health Records", Expert Systems with Applications, vol. 206, Jun. 23, 2022, (12 pages), doi. org/10.1016/j.eswa.2022.117932.
Wallace, et al., "Optum Labs: Building A Novel Node In The Learning Health Care System", Health Affairs, vol. 33, No. 7, pp. 1187-1194, (2014), doi: 10.1377/hlthaff.2014.0038.
Melnychuk, Valentyn, et al., "Causal Transformer for Estimating Counterfactual Outcomes", Proceedings of the 39th International Conference on Machine Learning, Jul. 17-23, 2022, 37 pages, Baltimore, Maryland.
Non-Final Rejection Mailed on Jun. 30, 2026 for U.S. Appl. No. 18/492,189, 44 page(s).

* cited by examiner

100
Client Computing Entities 102
Predictive Data Analysis Computing Entity 106
Storage Subsystem 108
Predictive Data Analysis System 101

TEMPORAL SEQUENCE CAUSAL TRANSFORMER MACHINE LEARNING MODEL

CROSS REFERENCE TO RELATED APPLICATION

This application claims the priority of U.S. Provisional Application No. 63/384,941, entitled "SCALABLE CLINICAL DECISION SUPPORT SYSTEMS USING TRANSFORMER ARCHITECTURES," filed on Nov. 23, 2022, the disclosure of which is hereby incorporated by reference in its entirety.

BACKGROUND

Various embodiments of the present disclosure address technical challenges related to performing predictive data analysis and provide solutions to address the efficiency and reliability shortcomings of existing predictive data analysis solutions.

BRIEF SUMMARY

In general, various embodiments of the present disclosure provide methods, apparatus, systems, computing devices, computing entities, and/or the like for performing predictive operations on an input temporal sequence.

In some embodiments, a computer-implemented method comprises: receiving, by one or more processors, an input temporal sequence, the input temporal sequence comprising one or more input tuples, at least one of the one or more input tuples comprising a plurality of tuple data objects comprising data representative of (a) one or more states, (b) one or more combinations of actions, (c) one or more outcomes, and (d) a cumulative discounted future outcome associated with the at least one of the one or more input tuples within the input temporal sequence; generating, by the one or more processors, a plurality of input tokens associated with the plurality of tuple data objects, the plurality of tokens generated according to a plurality of respective tuple data object types associated with the plurality of tuple data objects; generating, by the one or more processors and using a causal transformer machine learning model, a prediction output based on the plurality of input tokens and a conditional distribution of actions, the prediction output comprising a plurality of output tokens, wherein training the causal transformer machine learning model comprises: (a) projecting a plurality of training tokens into a plurality of respective embedding spaces using an embedding layer, wherein (i) at least one of embedding set, a structural embedding set, and a positional embedding set, (iii) the plurality of training tokens is associated with a plurality of training temporal sequences, and (iv) at least one of the plurality of training temporal sequences comprises one or more training tuples, wherein at least one of the one or more training tuples comprises a plurality of training tuple data objects comprising data representative of one or more training states, one or more training combinations of actions, one or more training outcomes, and a training cumulative discounted future outcome associated with the at least one of the one or more training tuples within the at least one of plurality of training temporal sequences, (b) inputting the plurality of respective embedding spaces into the causal transformer machine learning model, and (c) for at least one of the one or more training tuples, generating a context dependent representation based on one or more of the plurality of respective embedding spaces associated with sequentially prior ones of the one or more training tuples with respect to the at least one training tuple in the training temporal sequence; generating, by the one or more processors, one or more policy scores based on the prediction output; and initiating, by the one or more processors, the performance of one or more prediction-based actions based on the one or more policy scores and the prediction output.

In some embodiments, a computing apparatus comprising memory and one or more processors communicatively coupled to the memory, the one or more processors configured to: receive an input temporal sequence, the input temporal sequence comprising one or more input tuples, at least one of the one or more input tuples comprising a plurality of tuple data objects comprising data representative of (a) one or more states, (b) one or more combinations of actions, (c) one or more outcomes, and (d) a cumulative discounted future outcome associated with the at least one of the one or more input tuples within the input temporal sequence; generate a plurality of input tokens associated with the plurality of tuple data objects, the plurality of tokens generated according to a plurality of respective tuple data object types associated with the plurality of tuple data objects; generate, using a causal transformer machine learning model, a prediction output based on the plurality of input tokens and a conditional distribution of actions, the prediction output comprising a plurality of output tokens, wherein training the causal transformer machine learning model comprises: (a) projecting a plurality of training tokens into a plurality of respective embedding spaces using an embedding layer, wherein (i) at least one of embedding set, a structural embedding set, and a positional embedding set, (iii) the plurality of training tokens is associated with a plurality of training temporal sequences, and (iv) at least one of the plurality of training temporal sequences comprises one or more training tuples, wherein at least one of the one or more training tuples comprises a plurality of training tuple data objects comprising data representative of one or more training states, one or more training combinations of actions, one or more training outcomes, and a training cumulative discounted future outcome associated with the at least one of the one or more training tuples within the at least one of plurality of training temporal sequences, (b) inputting the plurality of respective embedding spaces into the causal transformer machine learning model, and (c) for at least one of the one or more training tuples, generating a context dependent representation based on one or more of the plurality of respective embedding spaces associated with sequentially prior ones of the one or more training tuples with respect to the at least one training tuple in the training temporal sequence; generate one or more policy scores based on the prediction output; and initiate the performance of one or more prediction-based actions based on the one or more policy scores and the prediction output.

In some embodiments, one or more non-transitory computer-readable storage media including instructions that, when executed by one or more processors, cause the one or more processors to receive an input temporal sequence, the input temporal sequence comprising one or more input tuples, at least one of the one or more input tuples comprising a plurality of tuple data objects comprising data representative of (a) one or more states, (b) one or more combinations of actions, (c) one or more outcomes, and (d) a cumulative discounted future outcome associated with the at least one of the one or more input tuples within the input temporal sequence; generate a plurality of input tokens associated with the plurality of tuple data objects, the plurality of tokens generated according to a plurality of respective tuple data object types associated with the plurality of tuple data objects; generate, using a causal transformer machine learning model, a prediction output based on the plurality of input tokens and a conditional distribution of actions, the prediction output comprising a plurality of output tokens, wherein training the causal transformer machine learning model comprises: (a) projecting a plurality of training tokens into a plurality of respective embedding spaces using an embedding layer, wherein (i) at least one of embedding set, a structural embedding set, and a positional embedding set, (iii) the plurality of training tokens is associated with a plurality of training temporal sequences, and (iv) at least one of the plurality of training temporal sequences comprises one or more training tuples, wherein at least one of the one or more training tuples comprises a plurality of training tuple data objects comprising data representative of one or more training states, one or more training combinations of actions, one or more training outcomes, and a training cumulative discounted future outcome associated with the at least one of the one or more training tuples within the at least one of plurality of training temporal sequences, (b) inputting the plurality of respective embedding spaces into the causal transformer machine learning model, and (c) for at least one of the one or more training tuples, generating a context dependent representation based on one or more of the plurality of respective embedding spaces associated with sequentially prior ones of the one or more training tuples with respect to the at least one training tuple in the training temporal sequence; generate one or more policy scores based on the prediction output; and initiate the performance of one or more prediction-based actions based on the one or more policy scores and the prediction output.

DETAILED DESCRIPTION

Figure 1:
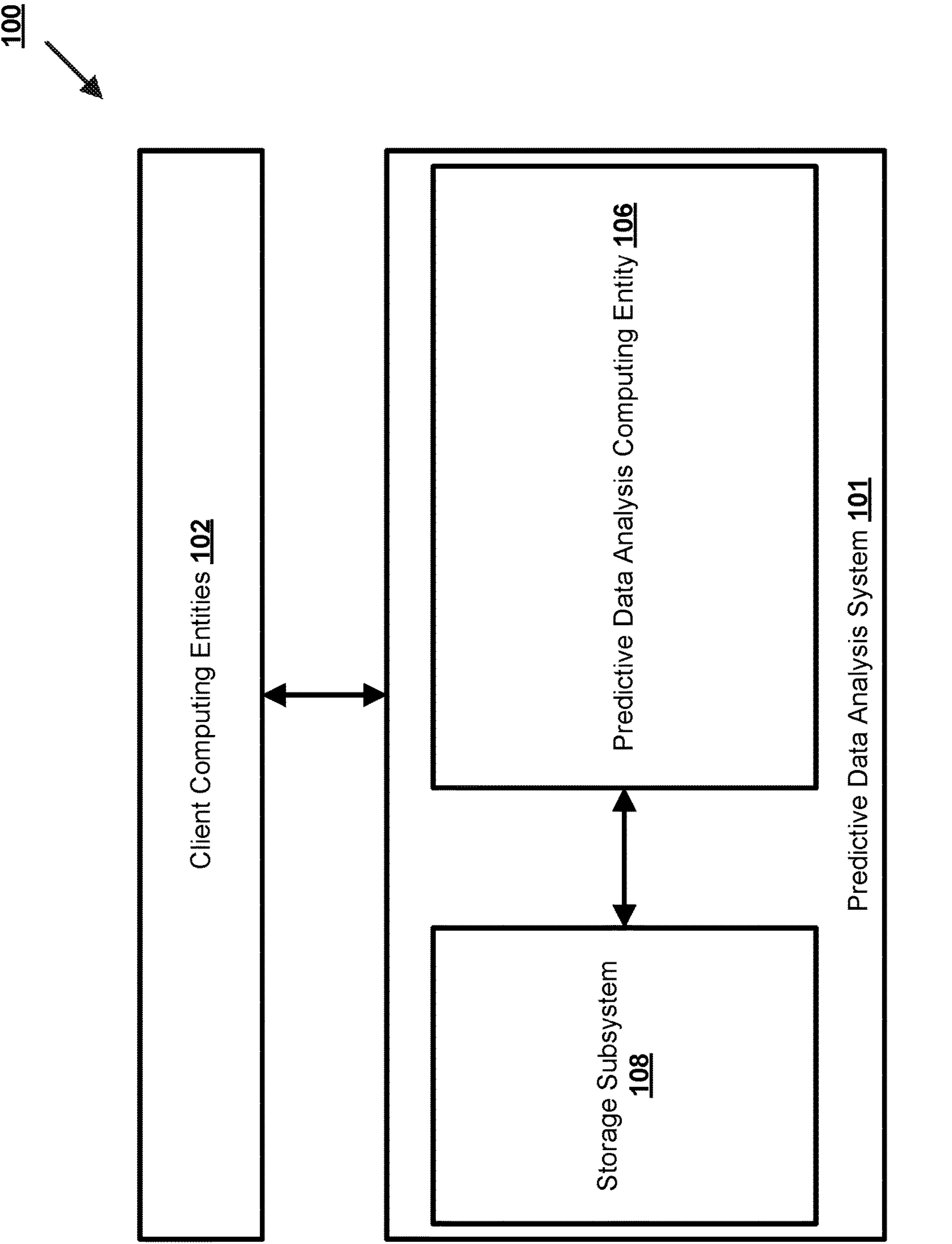
FIG. 1 provides an example overview of an architecture in accordance with some embodiments of the present disclosure.

Various embodiments of the present disclosure are described more fully hereinafter with reference to the accompanying drawings, in which some, but not all embodiments of the present disclosure are shown. Indeed, the present disclosure may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "example" are used to be examples with no indication of quality level. Terms such as "computing," "determining," "generating," and/or similar words are used herein interchangeably to refer to the creation, modification, or identification of data. Further, "based on," "based at least in part on," "based at least on," "based upon," and/or similar words are used herein interchangeably in an open-ended manner such that they do not necessarily indicate being based only on or based solely on the referenced element or elements unless so indicated. Like numbers refer to like elements throughout.

I. Computer Program Products, Methods, and Computing Entities

Embodiments of the present disclosure may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

A non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

A volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of an apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some example embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Example Framework

FIG. 1 is a schematic diagram of an example architecture 100 for performing predictive data analysis. The architecture 100 includes a predictive data analysis system 101 configured to receive predictive data analysis requests from client computing entities 102, process the predictive data analysis requests to generate predictions, provide the generated predictions to the client computing entities 102, and automatically initiate performance of prediction-based actions based on the generated predictions.

An example of a prediction-based action that can be performed using the predictive data analysis system 101 comprises troubleshooting a computing device based on a system log by predicting one or more diagnostic codes, one or more remedies (or a combination of remedies), one or more outcomes associated with performing the one or more remedies, and a cumulative discounted future outcome, displaying the one or more diagnostic codes, remedies, outcomes, and cumulative discounted future outcome on a user interface, and performing the one or more remedies. Another example of a prediction-based action that can be performed using the predictive data analysis system 101 comprises treating a patient based on electronic health record (EHR) data by predicting a patient's physiological state, a combination of treatments, one or more clinical outcomes associated with performing the combination of treatments, and a cumulative discounted future clinical outcome, displaying the physiological state, combination of treatments, clinical outcomes, and cumulative discounted future outcome on a user interface, and electronically facilitating the combination of treatments (e.g., communication, scheduling, or allocating resources). Other examples of prediction-based actions comprise generating a diagnostic report, displaying/providing resources, generating action scripts, generating alerts or reminders, or generating one or more electronic communications based on the predictions.

In accordance with various embodiments of the present disclosure, a causal transformer machine learning model may be trained to predict sequence elements following one or more prior sequence elements of a temporal sequence provided as input to the causal transformer machine learning model. A sequence element may comprise a tuple comprising a plurality of tuple data objects comprising data representative of states, combinations of actions, outcomes, and cumulative discounted future outcomes. As such, a sequence element may be used to represent a trajectory of events that occur sporadically, exhibit co-occurrences as dictated by situation, and occur at variable lengths of time between a first encounter and a last encounter. Accordingly, training the causal transformer machine learning model may comprise projecting a plurality of training tokens into a plurality of respective embedding spaces comprising a temporal embedding set, a structural embedding set, and a positional embedding set to capture the sporadicity of sequence elements as well as to account for heterogeneity in encounter patterns to differentiate between consecutive sequence elements that happen within a short timeframe to those that happened within a long timeframe. This technique will lead to higher accuracy of performing predictive operations as needed on certain sets of data and enable the causal transformer machine learning model to accurately predict future outcomes and a best combination of actions.

In some embodiments, predictive data analysis system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive predictive data analysis requests from one or more client computing entities 102, process the predictive data analysis requests to generate predictions corresponding to the predictive data analysis requests, provide the generated predictions to the client computing entities 102, and automatically initiate performance of prediction-based actions based on the generated predictions.

The storage subsystem 108 may be configured to store input data used by the predictive data analysis computing entity 106 to perform predictive data analysis as well as model definition data used by the predictive data analysis computing entity 106 to perform various predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

A. Example Predictive Data Analysis Computing Entity

Figure 2:
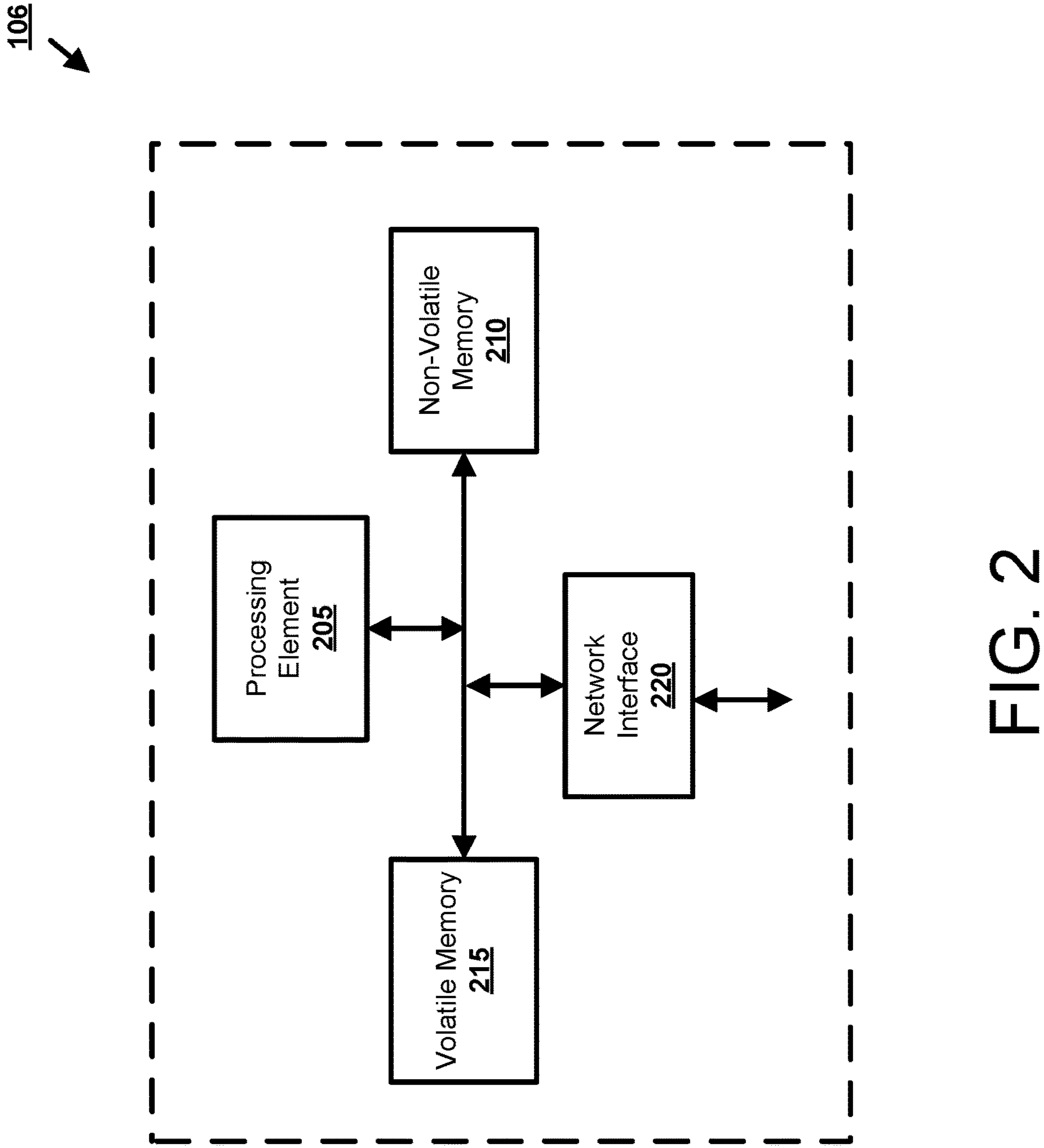
FIG. 2 provides an example predictive data analysis computing entity in accordance with some embodiments of the present disclosure.

FIG. 2 provides a schematic of a predictive data analysis computing entity 106 according to one embodiment of the present disclosure. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In some embodiments, these functions, operations, and/or processes can be performed on data, content, information, and/or similar terms used herein interchangeably.

As indicated, in some embodiments, the predictive data analysis computing entity 106 may also include one or more network interfaces 220 for communicating with various computing entities, such as by communicating data, content, information, and/or similar terms used herein interchangeably that can be transmitted, received, operated on, processed, displayed, stored, and/or the like.

As shown in FIG. 2, in some embodiments, the predictive data analysis computing entity 106 may include, or be in communication with, one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In some embodiments, the predictive data analysis computing entity 106 may further include, or be in communication with, non-volatile media (also referred to as non-volatile storage, memory, memory storage, memory circuitry and/or similar terms used herein interchangeably). In some embodiments, the non-volatile storage or memory may include one or more non-volatile memory 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In some embodiments, the predictive data analysis computing entity 106 may further include, or be in communication with, volatile media (also referred to as volatile storage, memory, memory storage, memory circuitry and/or similar terms used herein interchangeably). In some embodiments, the volatile storage or memory may also include one or more volatile memory 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in some embodiments, the predictive data analysis computing entity 106 may also include one or more network interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include, or be in communication with, one or more input elements, such as a keyboard input, a mouse input, a touch screen/display input, motion input, movement input, audio input, pointing device input, joystick input, keypad input, and/or the like. The predictive data analysis computing entity 106 may also include, or be in communication with, one or more output elements (not shown), such as audio output, video output, screen/display output, motion output, movement output, and/or the like.

B. Example Client Computing Entity

Figure 3:
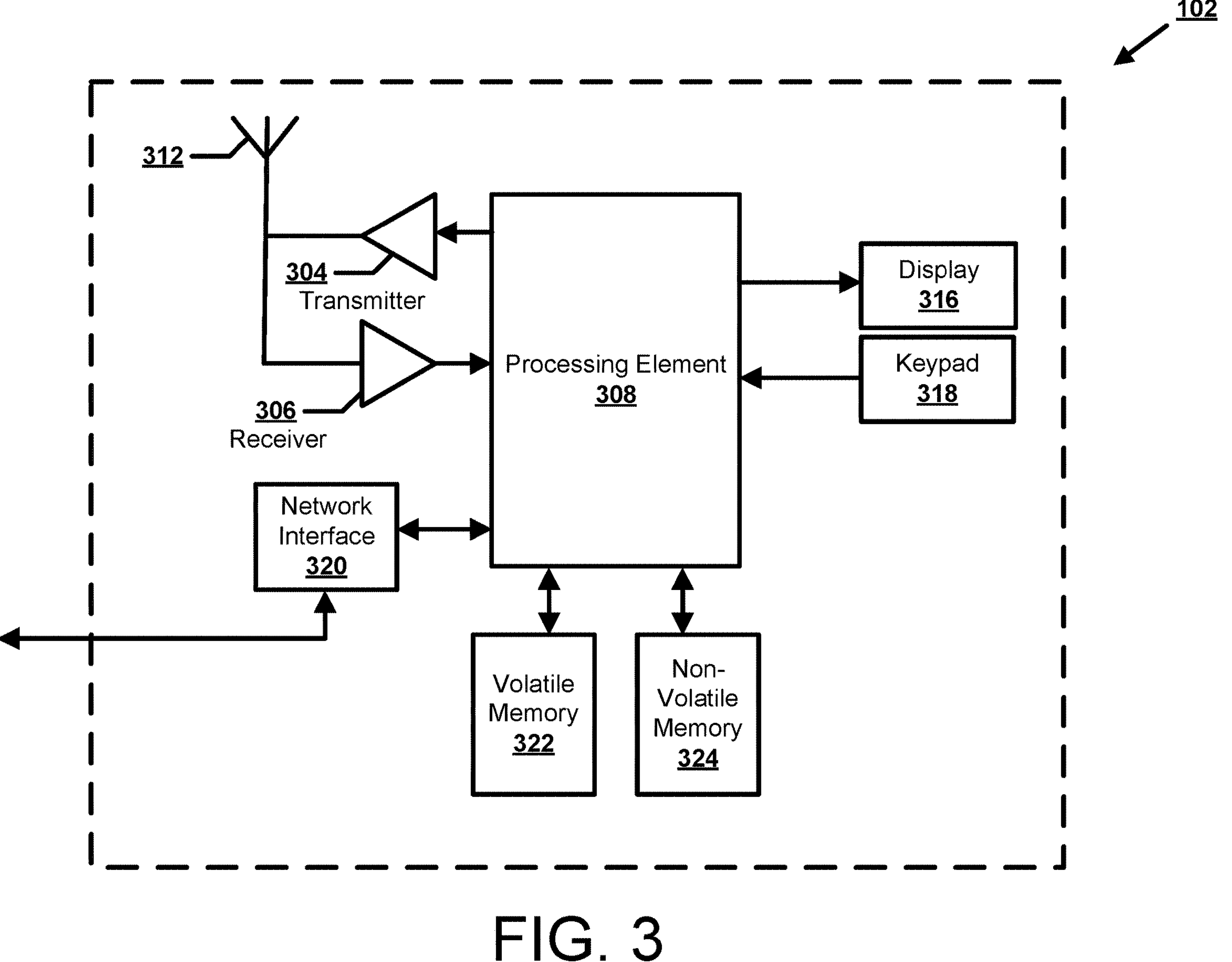
FIG. 3 provides an example client computing entity in accordance with some embodiments of the present disclosure.

FIG. 3 provides an illustrative schematic representative of a client computing entity 102 that can be used in conjunction with embodiments of the present disclosure. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the predictive data analysis computing entity 106. In some embodiments, the client computing entity 102 may operate in accordance with multiple wireless communication standards and protocols, such as UMTS, CDMA2000, 1xRTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the predictive data analysis computing entity 106 via a network interface 320.

Via these communication standards and protocols, the client computing entity 102 can communicate with various other entities using mechanisms such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to some embodiments, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In some embodiments, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the position of the client computing entity 102 in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the predictive data analysis computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile memory 322 and/or non-volatile memory 324, which can be embedded and/or may be removable. For example, the non-volatile memory 324 may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory 322 may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the client computing entity 102 or accessible through a browser or other user interface for communicating with the predictive data analysis computing entity 106 and/or various other computing entities.

In another embodiment, the client computing entity 102 may include one or more components or functionality that are the same or similar to those of the predictive data analysis computing entity 106, as described in greater detail above. As will be recognized, these architectures and descriptions are provided for example purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

III. Examples of Certain Terms

In some embodiments, the term “temporal sequence” may refer to a data construct that describes a time series of one or more tuples associated with instances of encounters with respected to an entity. According to some embodiments, a temporal sequence may comprise a sequence of one or more tuples, wherein each tuple may comprise a plurality of tuple data objects comprising data representative of states, combinations of actions, outcomes, and a cumulative discounted future outcome. In some embodiments, a temporal sequence may be provided to as a prediction input to a decision support machine learning model framework comprising a causal transformer machine learning model to generate a prediction output based on the temporal sequence. A temporal sequence may comprise data from images, text files, audio/video files, and application files. In one example, an entity may comprise a computing device and a temporal sequence may be generated from a system log comprising a time series of a plurality of tuple data objects associated with a computing device’s history of encounters (e.g., incidents, interactions, data access/modifications, infiltrations, or data exfiltration). In another example embodiment, an entity may comprise a medical patient and a temporal sequence may be derived or generated from electronic health records (EHRs)

comprising a time series of a plurality of tuple data objects associated with a patient's history of encounters (e.g., visits, admission, or meetings). As such, a temporal sequence may be representative of any entity's trajectory with respect to condition, treatment, and outcome over multiple encounter sessions.

In some embodiments, the term "tuple" may refer to a data construct that describes an element of a temporal sequence. As an example, a tuple may be representative of an encounter instance within a temporal sequence. A tuple may comprise a plurality of tuple data objects comprising data representative of states, combinations of actions, outcomes, and cumulative discounted future outcomes. For example, an encounter instance may be represented by a tuple comprising a plurality of tuple data objects in the form ($s_t$, $a_t$, $r_t$, $R_t$). Relative to a timestamp (t), s may represent a state (e.g., a computing device state, a diagnostic code, or a physical/physiological state), a may represent a combination of actions taken at the encounter instance, r may represent an outcome (e.g., increase in computing device performance, an improvement in condition, or a reduction in disease severity or inpatient stay occurring) after the combination of actions a was taken, and $R_t$ may represent a cumulative discounted future outcome. A cumulative discounted future outcome may comprise a sum of all discounted future outcomes in a temporal sequence associated with a tuple. In some embodiments, the cumulative discounted future outcome may be determined with a discount factor γ, e.g., $$R_t = \sum_{t'=t}^{T} \gamma^{t'} r_{t'}.$$

In another embodiment, the cumulative discounted future outcome may be windowed with a horizon parameter w, e.g., $$R_t = \sum_{t'=t}^{t+w} r_{t'}.$$

In some embodiments, the term "tuple data object" may refer to a data construct that describes an attribute of a tuple associated with an encounter instance within a temporal sequence. For example, a tuple of a temporal sequence may comprise a plurality of tuple data objects comprising data representative of (i) one or more states, (ii) one or more combinations of actions, (iii) one or more outcomes associated with a given one of the one or more states proceeding a respective one of the one or more combinations of actions, and (iv) a cumulative discounted future outcome associated with the tuple within the temporal sequence. A plurality of tuple data objects within a temporal sequence may be internally related and include correlations of various degrees that may be interpreted with various meanings. As an example, a tuple may represent a computing device incident on a given date and comprise a plurality of tuple data objects comprising data representative of one or more computing device status (state), one or more combination of actions, one or more computing device outcomes, and a cumulative discounted future computing device outcome associated with the computing device incident. As another example, a tuple may represent a patient admission on a given date and comprise a plurality of tuple data objects comprising data representative of one or more patient conditions (state), one or more combination of treatments (combination of actions), one or more clinical outcomes, and a cumulative discounted future clinical outcome associated with the patient admission.

In some embodiments, the term "token" may refer to a data construct that describes a unique representation of a tuple data object in a format suitable for processing by a machine learning model. For example, a token may comprise one or more integers and/or characters representative of features of a tuple data object. A token may be formatted according to integer values, binary values, or hexadecimal values. A tuple data object may be converted into a token using a predefined mapping of features associated with the tuple data object to the token. In some embodiments, a token may be generated for a tuple data object based on its tuple data object type (e.g., state, combination of actions, outcome, or cumulative discounted future outcome) represented by the tuple data object. For example, a token may be assigned to each specific combination of actions (e.g., individual, pairwise, or higher order) in a tuple comprising one or more tuple data objects comprising data representative of one or more combinations of actions. As another example, a token may be assigned to each state in a tuple comprising one or more tuple data objects comprising data representative of one or more states (such as, a unique token for each severity level or encounter type). In yet another example, a token may be assigned to each outcome or discounted future outcome in a tuple comprising one or more tuple data objects comprising data representative of one or more outcomes or discounted future outcomes. In some embodiments, tokenizing discounted future outcomes may comprise sampling the discounted future outcomes into discrete values by dividing the discount outcomes into M quantiles and mapping each quantile into a single token.

In some embodiments, the term "conditional distribution of actions" may refer to a data construct that describes a distribution of probability values associated with occurrence of a plurality of actions. In some embodiments, the conditional distribution may be generated by determining, for one or more states associated with a tuple of a temporal sequence, a number of action combination tokens that are present within the tuple associated with tuple data objects comprising data representative of a specific state. In some embodiments, one or more of the plurality of action combination tokens may be excluded from the conditional distribution of actions based on the excluded one or more action combination tokens including probability scores below a threshold. In some embodiments, the excluded one or more of the plurality of action combination tokens may be replaced with one or more action combination tokens comprising most frequent actions or actions coincident with the largest number of action combination tokens that are present within the tuple that are similar to the excluded one or more of the plurality of action combination tokens.

In some embodiments, the term "action space data object" may refer to a data construct that describes a list of individual actions comprising possible actions that may exist in combinations of actions associated with training temporal sequences and/or used to generate a prediction output by a causal transformer machine learning model. For example, an action space data object may be generated based on expert knowledge data, guidelines data, or databases associated with a given subject matter or comprising actions that may be present in temporal sequences. In some embodiments, an action space data object may be used to assign a plurality of action combination tokens to a plurality of combinations comprising possible actions from the action space data object.

In some embodiments, the term "decision support machine learning model framework" may refer to a data construct that describes parameters, hyperparameters, and/or defined operations of a machine learning model that is configured to receive an input temporal sequence comprising a plurality of tuple data objects, generate a plurality of input tokens associated with the plurality of tuple data objects, the plurality of tokens generated according to a plurality of respective tuple data object types associated with the plurality of tuple data objects, generate, using a causal transformer machine learning model, a prediction output based on the plurality of input tokens and a conditional distribution of actions, generate one or more policy scores based on the prediction output, and initiate the performance of one or more prediction-based actions based on the one or more policy scores and the prediction output.

In some embodiments, the term "causal transformer machine learning model" may refer to a data construct that describes parameters, hyperparameters, and/or defined operations of a machine learning model that is configured to predict one or more next elements (e.g., tuples) of a temporal sequence based on input of one or more previous elements of the temporal sequence. According to various embodiments of the present disclosure, a causal transformer machine learning model may predict a next tuple (e.g., comprising one or more output states, output combinations of actions, output outcomes, and an output cumulative discounted future outcome) of a temporal sequence based on one or more input tuples (e.g., each input tuple comprising one or more states, combinations of actions, outcomes, and an cumulative discounted future outcome associated with an encounter instance) of the temporal sequence. A causal transformer machine learning model may further predict additional tuples by iteratively adding predicted tuples to the temporal sequence using the updated temporal sequence as input for prediction of the additional tuples. In one example embodiment, a causal transformer machine learning model may be trained based on teacher-forcing training by using one or more ground-truth tokens as training feedback input to the causal transformer machine learning model. In some embodiments, a causal transformer machine learning model may comprise a generative pre-trained transformer machine learning model. According to one embodiment of the present disclosure, training a causal transformer machine learning model comprises (a) projecting a plurality of training tokens into a plurality of respective embedding spaces using an embedding layer, wherein (i) at least one of the plurality of respective embedding spaces comprises a plurality of embedding sets associated with the plurality of training tokens, (ii) the plurality of embedding sets comprises a temporal embedding set, a structural embedding set, and a positional embedding set, (iii) the plurality of training tokens is associated with a plurality of training temporal sequences, and (iv) at least one of the plurality of training temporal sequences comprises one or more training tuples, wherein each training tuple may comprise a plurality of training tuple data objects comprising data representative of (1) one or more training states, (2) one or more training combinations of actions, (3) one or more training outcomes associated with a given one of the one or more training states proceeding a respective one of the one or more training combinations of actions, and (4) a training cumulative discounted future outcome associated with a given one of the one or more training tuples within the at least one of plurality of training temporal sequences, (b) inputting the plurality of respective embedding spaces into the causal transformer machine learning model, and (c) for at least one of the one or more training tuples, generating a context dependent representation based on one or more of the plurality of respective embedding spaces associated with sequentially prior ones of the one or more training tuples with respect to the at least one training tuple in the training temporal sequence. In some embodiments, during training, the training cumulative discounted future outcome may be masked to prevent leakage of information from the future while learning to predict an output combination of actions $$\{a_{t'}\}_{t'=t+1}^{T}$$

or an output state $$\{S_{t'}\}_{t'=t+1}^{T}.$$

In some embodiments, the term "prediction output" may refer to a data construct that describes output generated by a causal transformer machine learning model. According to various embodiments of the present disclosure, a causal transformer machine learning model may generate a prediction output based on a plurality of input tokens and a conditional distribution of actions. A prediction output may comprise a plurality of output tokens. In some embodiments, the plurality of output tokens may comprise one or more output state tokens (representative of one or output states), one or more output combinations of actions tokens (representative of one or more output combinations of actions), one or more output outcome tokens (representative of one or more output outcomes), and an output cumulative discounted future outcome token (representative of an output cumulative discounted future outcome). In some embodiments, generating the prediction output may further comprise generating one or more log-likelihood scores of one or more output combinations of actions associated with the one or more output combinations of actions tokens, wherein the log-likelihood scores are representative of a likelihood of the one or more output combinations of actions most likely to follow based on an input temporal sequence. In some embodiments, generating the prediction output may further comprise generating one or more predictive scores, wherein the one or more predictive scores comprises (i) one or more action predictive scores of one or more output combinations of actions associated with the one or more output combinations of actions tokens based on the one or more states, and (ii) one or more outcome predictive scores associated with an output cumulative discounted future outcome associated with the output cumulative discounted future outcome token based on the one or more output combinations of actions. In some embodiments, generating the prediction output may further comprise generating one or more expected predicted outcomes based on the output cumulative discounted future outcome and the one or more predictive scores. In some embodiments, at least one sequentially first ones of the one or more training tuples may be discarded from one or more of the plurality of training temporal sequences.

In some embodiments, the term "training temporal sequence" may refer to a data construct that describes a time series of one or more training tuples associated with instances of training encounters used for training a causal transformer machine learning model. According to some embodiments, a training temporal sequence may comprise a sequence of one or more training tuples, where each training tuple comprises a plurality of training tuple data objects comprising data representative of training states, training combinations of actions, training outcomes, and a training cumulative discounted future outcome.

In some embodiments, the term "training tuple" may refer to a data construct that describes a training encounter instance within a training temporal sequence. A training tuple may comprise a plurality of training tuple data objects comprising data representative of training states, training combinations of actions, training outcomes, or a training cumulative discounted future outcome. In some embodiments, the one or more training outcomes may be associated with a given one of the one or more training states proceeding a respective one of the one or more training combinations of actions. In some embodiments, the training cumulative discounted future outcome may be associated with a given one of the one or more training tuples within the at least one of plurality of training temporal sequences.

In some embodiments, the term "training tuple data object" may refer to a data construct that describes an attribute of a tuple associated with a training encounter instance within a training temporal sequence. For example, a training tuple of a training temporal sequence may comprise a plurality of training tuple data objects comprising data representative of (i) one or more training states, (ii) one or more training combinations of actions, (iii) one or more training outcomes associated with a given one of the one or more training states proceeding a respective one of the one or more training combinations of actions, and (iv) a training cumulative discounted future outcome associated with the training tuple within the training temporal sequence.

In some embodiments, the term "temporal embedding set" may refer to a data construct that describes one or more embeddings associated with a relative time between one of a plurality of training tuple data objects and a sequentially first one of the plurality of training tuple data objects in one of a plurality of training temporal sequences.

In some embodiments, the term "structural embedding set" may refer to a data construct that describes one or more embeddings associated with a plurality of respective tuple data object types of a plurality of training tuple data objects.

In some embodiments, the term "positional embedding set" may refer to a data construct that describes one or more embeddings associated with a sequential position of one of a plurality of training tuple data objects in one of a plurality of training temporal sequences.

In some embodiments, the term "context dependent representation" may refer to a data construct that describes an attention mechanism applied in a causal transformer machine learning model for weighting training tuples within a training temporal sequence during training of the causal transformer machine learning model. A causal transformer machine learning model may use a context dependent representation to interpret data from one or more training tuples for generating a prediction output. According to various embodiments of the present disclosure, for at least one (e.g., a training interval) of one or more training tuples, a context dependent representation may be generated based on one or more of the plurality of respective embedding spaces associated with sequentially prior ones of the one or more training tuples with respect to the at least one training tuple in the training temporal sequence.

In some embodiments, the term "policy score" may refer to a data construct that describes an evaluative quantification of an action (or a combination of actions) representative of a suggestion of the action (or combination of actions). According to various embodiments of the present disclosure, one or more policy scores may be generated for one or more respective combinations of actions associated with a prediction output generated by a causal transformer machine learning model. In some embodiments, the performance of one or more prediction-based actions may be initiated based on the one or more policy scores and the prediction output. In some embodiments, one or more output combinations of actions (e.g., associated with one or more output combination of actions tokens of a prediction output generated by a causal transformer machine learning model) may be selected for recommendation based on one or more policy scores.

IV. Overview, Technical Improvements, and Technical Advantages

Various embodiments of the present disclosure make important technical contributions to improving predictive accuracy of causal transformer machine learning models by using a combination of temporal, structural, and positional embeddings to characterize temporal sequences comprising one or more tuples representative of one or more respective encounter instances. This approach improves training speed and training efficiency of training causal transformer machine learning models. It is well-understood in the relevant art that there is typically a tradeoff between predictive accuracy and training speed, such that it is trivial to improve training speed by reducing predictive accuracy. Thus, the challenge is to improve training speed without sacrificing predictive accuracy through innovative model architectures. Accordingly, techniques that improve predictive accuracy without harming training speed, such as the techniques described herein, enable improving training speed given a constant predictive accuracy. In doing so, the techniques described herein improve efficiency and speed of training causal transformer machine learning models, thus reducing the number of computational operations needed and/or the amount of training data entries needed to train causal transformer machine learning models. Accordingly, the techniques described herein improve the computational efficiency, storage-wise efficiency, and/or speed of training machine learning models.

For example, various embodiments of the present disclosure improve predictive accuracy of causal transformer machine learning models by using a combination of temporal, structural, and positional embeddings to characterize tuples representative of encounter instances within a temporal sequence. As described herein, a tuple may comprise features representative of various states, combination of actions, outcomes, and a cumulative discounted future outcome, which may be sporadic, varied and/or repetitive. For this reason, it is important to have techniques available to capture the nature of such features in a tuple.

However, in accordance with various embodiments of the present disclosure, a causal transformer machine learning model may be trained to predict sequence elements following one or more prior sequence elements of a temporal sequence provided as input to the causal transformer machine learning model. A sequence element may comprise a tuple comprising a plurality of tuple data objects comprising data representative of states, combinations of actions, outcomes, and cumulative discounted future outcomes. As such, a sequence element may be used to represent a trajectory of events that occur sporadically, exhibit co-occurrences as dictated by situation, and occur at variable lengths of time between a first encounter and a last encounter. Accordingly, training the causal transformer machine learning model may comprise projecting a plurality of training tokens into a plurality of respective embedding spaces comprising a temporal embedding set, a structural embedding set, and a positional embedding set to capture the sporadicity of sequence elements as well as to account for heterogeneity in encounter patterns to differentiate between consecutive sequence elements that happen within a short timeframe to those that happened within a long timeframe. This technique will lead to higher accuracy of performing predictive operations as needed on certain sets of data and enable the causal transformer machine learning model to accurately predict future outcomes and a best combination of actions.

Furthermore, machine learning models that generate recommendations (prediction output) that are opaque as to the reasoning behind them are not useful, for example, in a critical setting where there is a need to justify the reasoning for certain action decisions. Using such opaque machine learning models saves end-users little if any time because an end-user may repeat most of the work done by a machine learning model simply to determine why the machine learning model yielded a certain recommendation. Accordingly, techniques for evaluating model mechanisms to explain its recommendations to end-user are also disclosed herewith.

V. Example System Operations

As indicated, various embodiments of the present disclosure make important technical contributions to improving predictive accuracy of causal transformer machine learning models by using a combination of temporal, structural, and positional embeddings to characterize temporal sequences comprising one or more tuples representative of one or more respective encounter instances. This approach improves training speed and training efficiency of training causal transformer machine learning models. It is well-understood in the relevant art that there is typically a tradeoff between predictive accuracy and training speed, such that it is trivial to improve training speed by reducing predictive accuracy. Thus, the challenge is to improve training speed without sacrificing predictive accuracy through innovative model architectures. Accordingly, techniques that improve predictive accuracy without harming training speed, such as the techniques described herein, enable improving training speed given a constant predictive accuracy. In doing so, the techniques described herein improve efficiency and speed of training causal transformer machine learning models, thus reducing the number of computational operations needed and/or the amount of training data entries needed to train causal transformer machine learning models. Accordingly, the techniques described herein improve the computational efficiency, storage-wise efficiency, and/or speed of training machine learning models.

Figure 4:
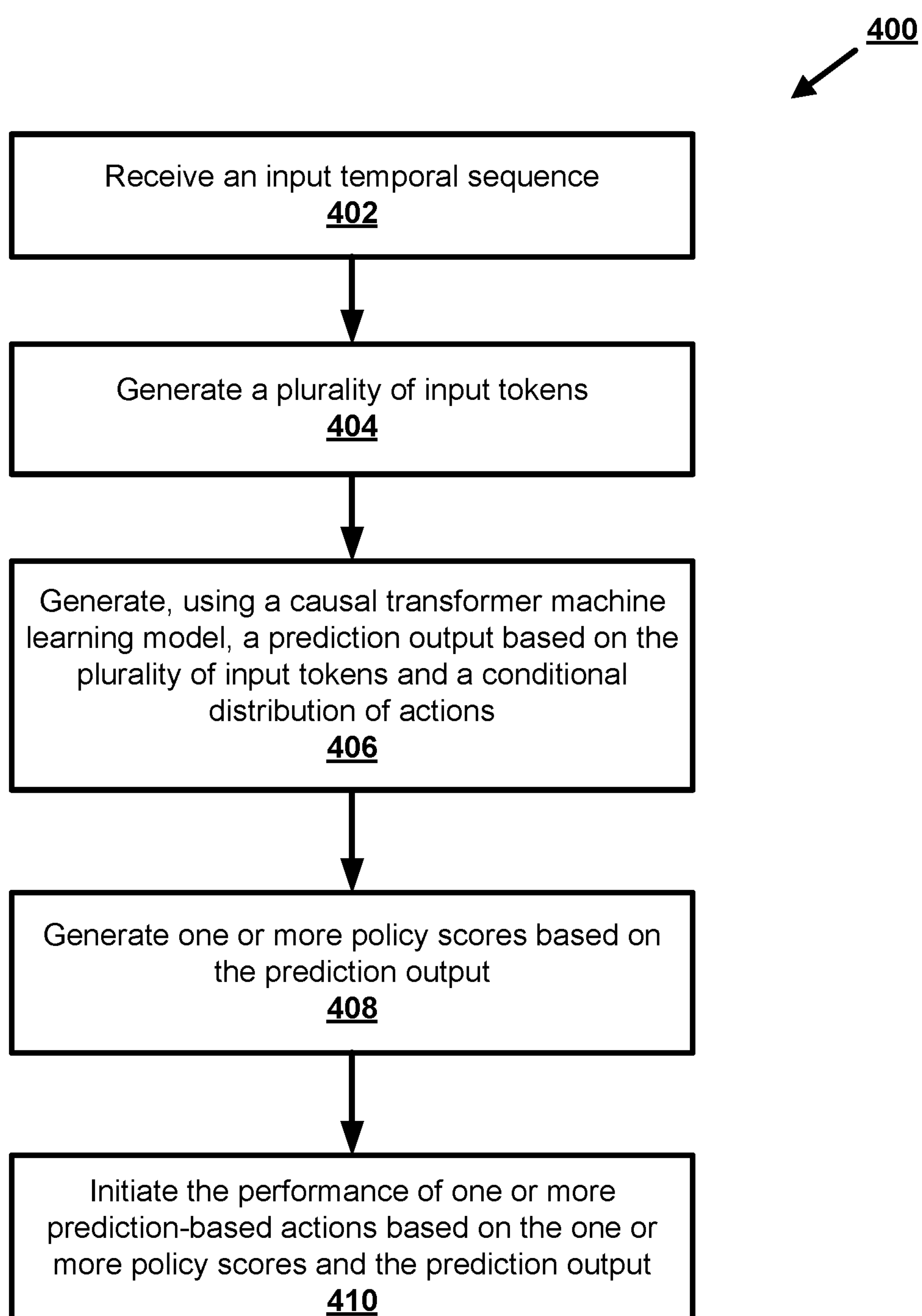
FIG. 4 is a flowchart diagram of an example process for performing predictive operations on an input temporal sequence in accordance with some embodiments of the present disclosure.

FIG. 4 is a flowchart diagram of an example process 400 for performing predictive operations on an input temporal sequence. In some embodiments, via the various steps/operations of the process 400, the predictive data analysis computing entity 106 can use a decision support machine learning model framework to generate a prediction output for an input temporal sequence and use the prediction to generate one or more policy scores for selecting actions for recommendation to improve or provide a desired outcome.

In some embodiments, the process 400 begins at step/operation 402 when the predictive data analysis computing entity 106 receives an input temporal sequence. The input temporal sequence may comprise one or more input tuples and at least one of the one or more input tuples may comprise a plurality of tuple data objects. The plurality of tuple data objects may comprise data representative of one or more states, one or more combinations of actions, one or more outcomes, and a cumulative discounted future outcome associated with the at least one of the one or more input tuples within the input temporal sequence.

In some embodiments, a temporal sequence describes a time series of one or more tuples associated with instances of encounters with respected to an entity. According to some embodiments, a temporal sequence may comprise a sequence of one or more tuples. In some embodiments, a temporal sequence may be provided to as a prediction input to a decision support machine learning model framework comprising a causal transformer machine learning model to generate a prediction output based on the temporal sequence. A temporal sequence may comprise data from images, text files, audio/video files, and application files. In one example, an entity may comprise a computing device and a temporal sequence may be generated from a system log comprising a time series of a plurality of tuple data objects associated with a computing device's history of encounters (e.g., incidents, interactions, data access/modifications, infiltrations, or data exfiltration). In another example embodiment, an entity may comprise a medical patient and a temporal sequence may be derived or generated from electronic health records (EHRs) comprising a time series of a plurality of tuple data objects associated with a patient's history of encounters (e.g., visits, admission, or meetings). As such, a temporal sequence may be representative of any entity's trajectory with respect to condition, treatment, and outcome over multiple encounter sessions.

In some embodiments, a tuple describes an element of a temporal sequence. As an example, a tuple may be representative of an encounter instance within a temporal sequence. A tuple may comprise a plurality of tuple data objects comprising data representative of states, combinations of actions, outcomes, and cumulative discounted future outcomes. For example, an encounter instance may be represented by a tuple comprising a plurality of tuple data objects in the form ($s_t$, $a_t$, $r_t$, $R_t$). Relative to a timestamp (t), s may represent a state (e.g., a computing device state, a diagnostic code, or a physical/physiological state), a may represent a combination of actions taken at the encounter instance, r may represent an outcome (e.g., increase in computing device performance, an improvement in condition, a reduction in disease severity, or inpatient stay occurring) after the combination of actions a was taken, and $R_t$ may represent a cumulative discounted future outcome. A cumulative discounted future outcome may comprise a sum of all discounted future outcomes in a temporal sequence associated with a tuple. In some embodiments, the cumulative discounted future outcome may be determined with a discount factor γ, e.g., $$R_t = \sum_{t'=t}^{T} \gamma^{t'} r_{t'}.$$

In another embodiment, the cumulative discounted future outcome may be windowed with a horizon parameter w, e.g., $$R_t = \sum_{t'=t}^{t+w} r_{t'}.$$

In some embodiments, a tuple data object describes an attribute of a tuple associated with an encounter instance within a temporal sequence. For example, a tuple of a temporal sequence may comprise a plurality of tuple data objects comprising data representative of (i) one or more states, (ii) one or more combinations of actions, (iii) one or more outcomes associated with a given one of the one or more states proceeding a respective one of the one or more combinations of actions, and (iv) a cumulative discounted future outcome associated with the tuple within the temporal sequence. A plurality of tuple data objects within a temporal sequence may be internally related and include correlations of various degrees that may be interpreted with various meanings. As an example, a tuple may represent a computing device incident on a given date and comprise a plurality of tuple data objects comprising data representative of one or more computing device status (state), one or more combination of actions, one or more computing device outcomes, and a cumulative discounted future computing device outcome associated with the computing device incident. As another example, a tuple may represent a patient admission on a given date and comprise a plurality of tuple data objects comprising data representative of one or more patient conditions (state), one or more combination of treatments (combination of actions), one or more clinical outcomes, and a cumulative discounted future clinical outcome associated with the patient admission.

As described herein, in accordance with various embodiments of the present disclosure, a causal transformer machine learning model may be trained to predict sequence elements following one or more prior sequence elements of a temporal sequence provided as input to the causal transformer machine learning model. A sequence element may comprise a tuple comprising a plurality of tuple data objects comprising data representative of states, combinations of actions, outcomes, and cumulative discounted future outcomes. As such, a sequence element may be used to represent a trajectory of events that occur sporadically, exhibit co-occurrences as dictated by situation, and occur at variable lengths of time between a first encounter and a last encounter. Accordingly, training the causal transformer machine learning model may comprise projecting a plurality of training tokens into a plurality of respective embedding spaces comprising a temporal embedding set, a structural embedding set, and a positional embedding set to capture the sporadicity of sequence elements as well as to account for heterogeneity in encounter patterns to differentiate between consecutive sequence elements that happen within a short timeframe to those that happened within a long timeframe. This technique will lead to higher accuracy of performing predictive operations as needed on certain sets of data and enable the causal transformer machine learning model to accurately predict future outcomes and a best combination of actions.

In some embodiments, at step/operation 404, the predictive data analysis computing entity 106 generates a plurality of input tokens associated with the plurality of tuple data objects, the plurality of tokens generated according to a plurality of respective tuple data object types associated with the plurality of tuple data objects. In some embodiments, a token describes a unique representation of a tuple data object in a format suitable for processing by a machine learning model. For example, a token may comprise one or more integers and/or characters representative of features of a tuple data object. A token may be formatted according to integer values, binary values, or hexadecimal values. A tuple data object may be converted into a token using a predefined mapping of features associated with the tuple data object to the token. In some embodiments, generating the plurality of input tokens may further comprises receiving an action space data object comprising a plurality of possible individual actions, and assigning a plurality of action combination tokens to a plurality of combinations comprising selected ones of the plurality of possible individual actions.

In some embodiments, a token may be generated for a tuple data object based on its tuple data object type (e.g., state, combination of actions, outcome, or cumulative discounted future outcome) represented by the tuple data object. For example, a token may be assigned to each specific combination of actions (e.g., individual, pairwise, or higher order) in a tuple comprising one or more tuple data objects comprising data representative of one or more combinations of actions. As another example, a token may be assigned to each state in a tuple comprising one or more tuple data objects comprising data representative of one or more states (such as, a unique token for each severity level or encounter type). In yet another example, a token may be assigned to each outcome or discounted future outcome in a tuple comprising one or more tuple data objects comprising data representative of one or more outcomes or discounted future outcomes. In some embodiments, tokenizing discounted future outcomes may comprise sampling the discounted future outcomes into discrete values by dividing the discount outcomes into M quantiles and mapping each quantile into a single token.

In some embodiments, at step/operation 406, the predictive data analysis computing entity 106 generates, using a causal transformer machine learning model, a prediction output based on the plurality of input tokens and a conditional distribution of actions.

In some embodiments, a conditional distribution of actions describes a distribution of probability values associated with occurrence of a plurality of actions. In some embodiments, the conditional distribution may be generated based on one or more states associated with a temporal sequence. In some embodiments, the conditional distribution may be generated by determining, for one or more states associated with a tuple of a temporal sequence, a number of action combination tokens that are present within the tuple associated with tuple data objects comprising data representative of a specific state. In some embodiments, one or more of the plurality of action combination tokens may be excluded from the conditional distribution of actions based on the excluded one or more action combination tokens including probability scores below a threshold. In some embodiments, the excluded one or more of the plurality of action combination tokens may be replaced with one or more action combination tokens comprising most frequent actions or actions coincident with the largest number of action combination tokens that are present within the tuple that are similar to the excluded one or more of the plurality of action combination tokens.

In some embodiments, an action space data object describes a list of individual actions comprising possible actions that may exist in combinations of actions associated with training temporal sequences and/or used to generate a prediction output by a causal transformer machine learning model. For example, an action space data object may be generated based on expert knowledge data, guidelines data, or databases associated with a given subject matter or comprising actions that may be present in temporal sequences. In some embodiments, an action space data object may be used to assign a plurality of action combination tokens to a plurality of combinations comprising possible actions from the action space data object.

In some embodiments, a causal transformer machine learning model describes parameters, hyperparameters, and/ or defined operations of a machine learning model that is configured to predict one or more next elements (e.g., tuples) of a temporal sequence based on input of one or more previous elements of the temporal sequence. According to various embodiments of the present disclosure, a causal transformer machine learning model may predict a next tuple (e.g., comprising one or more output states, output combinations of actions, output outcomes, and an output cumulative discounted future outcome) of a temporal sequence based on one or more input tuples (e.g., each input tuple comprising one or more states, combinations of actions, outcomes, and an cumulative discounted future outcome associated with an encounter instance) of the temporal sequence. A causal transformer machine learning model may further predict additional tuples by iteratively adding predicted tuples to the temporal sequence using the updated temporal sequence as input for prediction of the additional tuples. In one example embodiment, a causal transformer machine learning model may be trained based on teacher-forcing training by using one or more ground-truth tokens as training feedback input to the causal transformer machine learning model. In some embodiments, a causal transformer machine learning model may comprise a generative pre-trained transformer machine learning model.

In some embodiments, a prediction output describes output generated by a causal transformer machine learning model. A prediction output may comprise a plurality of output tokens. In some embodiments, the plurality of output tokens may comprise one or more output state tokens (representative of one or output states), one or more output combinations of actions tokens (representative of one or more output combinations of actions), one or more output outcome tokens (representative of one or more output outcomes), and an output cumulative discounted future outcome token (representative of an output cumulative discounted future outcome).

In some embodiments, generating the prediction output may further comprise generating one or more log-likelihood scores of one or more output combinations of actions associated with the one or more output combinations of actions tokens, wherein the log-likelihood scores are representative of a likelihood of the one or more output combinations of actions most likely to follow based on an input temporal sequence. As an example, for a sequence r of length T, a prediction output of the causal transformer machine learning model with parameters θ may comprise the induced log-likelihood:

$$\ell\ell_\theta(\tau) = \sum_{t=1}^{T}\left(\sum_{i=1}^{M}\log P_\theta\left(s_t^i \mid s_t^{<i}, \tau_{<t}\right) + \log P_\theta(a_t \mid s_t, \tau_{<t}) + \log P_\theta(R_t \mid s_t, a_t, \tau_{<t})\right) \quad \text{Equation 1}$$

In the above equation, M may represent the states dimension and $\tau_{<t}$ may represent all items of the sequence τ that appeared before time t. Using this property, it is possible to generate log-likelihood scores that are attribute specific such as the following actions log-likelihood:

$$\ell\ell_\theta^{\mathcal{A}}(\tau) = \sum_{j=t}^{T}\log P_\theta(a_t \mid s_t, \tau_{<t}) \quad \text{Equation 2}$$

Assuming statistical independence between temporal sequences, log-likelihood scores for an entire cohort D may be generated by the following Equations 3 and 4:

$$\ell\ell_\theta(D) = \sum_{i=1}^{N}\ell\ell_\theta\left(\tau^{(i)}\right) \quad \text{Equation 3}$$

$$\ell\ell_\theta^{\mathcal{A}}(D) = \sum_{i=1}^{N}\ell\ell_\theta^{\mathcal{A}}\left(\tau^{(i)}\right) \quad \text{Equation 4}$$

In Equations 3 and 4, $\tau^{(i)}$ may represent a temporal sequence of the i-th entity (e.g., computing device, subject, patient) and N may represent the number of entities in the cohort.

In some embodiments, generating the prediction output may further comprise generating one or more predictive scores, wherein the one or more predictive scores comprises (i) one or more action predictive scores of one or more output combinations of actions associated with the one or more output combinations of actions tokens based on the one or more states, and (ii) one or more outcome predictive scores associated with an output cumulative discounted future outcome associated with the output cumulative discounted future outcome token based on the one or more output combinations of actions.

The following Equations 5 and 6 may be used to generate prediction scores for actions and outcomes, respectively:

$$\ell_\theta(a_t; S_t, \tau_{<t}) = P_\theta(a_t|S_t, \tau_{<t}) \quad \text{Equation 5}$$

$$\ell_\theta(R_t; a_t, s_t, \tau_{<1}) = P_\theta(R_t|a_t, s_t, \tau_{<t}) \quad \text{Equation 6}$$

The above prediction scores may represent an estimated predictive distribution induced by the causal transformer machine learning model for observing different actions or outcomes (respectively) at time t given previously observed trajectory $\tau_{<t}$, and current available data (e.g., from the input temporal sequence).

In some embodiments, generating the prediction output may further comprise generating one or more expected predicted outcomes based on the output cumulative discounted future outcome and the one or more predictive scores. In some embodiments, at least one sequentially first ones of the one or more training tuples may be discarded from one or more of the plurality of training temporal sequences.

Using the outcome prediction score $\ell_\theta(R_t; a_t, s_t, \tau_{<t})$ described above, an estimated expected outcome $\hat{R}_t$ may be obtained for entity i with temporal sequence $\tau^{(i)}$, state $s_t$, and actions $a_t$ according to the following:

$$\hat{R}_t = \hat{R}(a_t; s_t, \tau_{<t}) = \mathbb{E}[R_\theta(a_t; s_t, \tau_{<t})] = \sum_{R_t \in \mathcal{R}} R_t \cdot \ell_\theta(R_t; a_t, s_t, \tau_{<t}) \quad \text{Equation 7}$$

In the above equation, $\mathcal{R}$ may represent all possible outcomes and $\ell_\theta(R_t; a_t, s_t, \tau_{<t})$ may represent the estimated probability to observe cumulative discounted future outcome R induced by the causal transformer machine learning model.

In some embodiments, at step/operation 408, the predictive data analysis computing entity 106 generates one or more policy scores based on the prediction output. In some embodiments, a policy score describes an evaluative quantification of an action (or a combination of actions) representative of a suggestion of the action (or combination of actions). According to various embodiments of the present disclosure, one or more policy scores may be generated for one or more respective combinations of actions associated with a prediction output generated by a causal transformer machine learning model. In some embodiments, the performance of one or more prediction-based actions may be initiated based on the one or more policy scores and the prediction output. In some embodiments, one or more output combinations of actions (e.g., associated with one or more output combination of actions tokens of a prediction output generated by a causal transformer machine learning model) may be selected for recommendation based on one or more policy scores.

In some embodiments, one or more policy scores may be generated by obtaining a predictive score, such as a log-likelihood score, for each possible action and identifying actions that are likely to appear in a next step of a sequence comprising a combination of the possible actions. Predictive scores for a plurality of possible combinations of actions are used to generate an action prediction probability distribution. Selected ones of the plurality of combinations of actions may be sampled from the action prediction probability distribution and expected predicted outcomes (e.g., generated by a causal transformer machine learning model as a prediction output) may be determined for each sampled combination of actions. In some embodiments, selection of the combinations of actions for sampling may be based on the selected combinations of actions comprising predictive scores that satisfy a given probability threshold. In another embodiment, the selected combinations of actions may be selected randomly or semi-randomly. One or more policy scores may be generated as a probability distribution over the selected combinations of actions sorted by outcome, for example, using the following equation:

$$\pi^*(a_t; s_t, \tau_{<t}) = \begin{cases} softmax(\hat{R}(a_t; s_t, \tau_{<t})) & a_t \in \hat{\mathcal{A}}_t^{(i)} \\ \epsilon & a_t \notin \hat{\mathcal{A}}_t^{(i)} \end{cases} \quad \text{Equation 8}$$

According to Equation 8, each action a t may be assigned with a suggestion score $\pi(a_t; s_t, \tau_{<t})$ representative of how likely the action is to be performed given current state $s_t$ and the quality of the expected future outcome $\hat{R}$ if the given action is performed. As such, the one or more policy scores may be used to determine combinations of actions comprising the best predicted outcomes.

In some embodiments, at step/operation 410, the predictive data analysis computing entity 106 initiates the performance of one or more prediction-based actions based on the one or more policy scores and the prediction output. Initiating the performance of the one or more prediction-based actions comprises, for example, performing a resource-based action (e.g., allocation of resource), generating a diagnostic report, generating action scripts, generating alerts or messages, and/or generating one or more electronic communications. The one or more prediction-based actions may further include displaying visual renderings of the aforementioned examples of prediction-based actions in addition to values, charts, and representations associated with the one or more policy scores and the prediction output using a prediction output user interface.

An example of a prediction-based action that can be performed using the predictive data analysis system 101 comprises troubleshooting a computing device based on a system log by predicting one or more diagnostic codes, one or more remedies (or a combination of remedies), one or more outcomes associated with performing the one or more remedies, and a cumulative discounted future outcome, displaying the one or more diagnostic codes, remedies, outcomes, and cumulative discounted future outcome on a user interface, and performing the one or more remedies. Another example of a prediction-based action that can be performed using the predictive data analysis system 101 comprises treating a patient based on electronic health record (EHR) data by predicting a patient's physiological state, a combination of treatments, one or more clinical outcomes associated with performing the combination of treatments, and a cumulative discounted future clinical outcome, displaying the physiological state, combination of treatments, clinical outcomes, and cumulative discounted future outcome on a user interface, and electronically facilitating the combination of treatments (e.g., communication, scheduling, or allocating resources).

Figure 5:
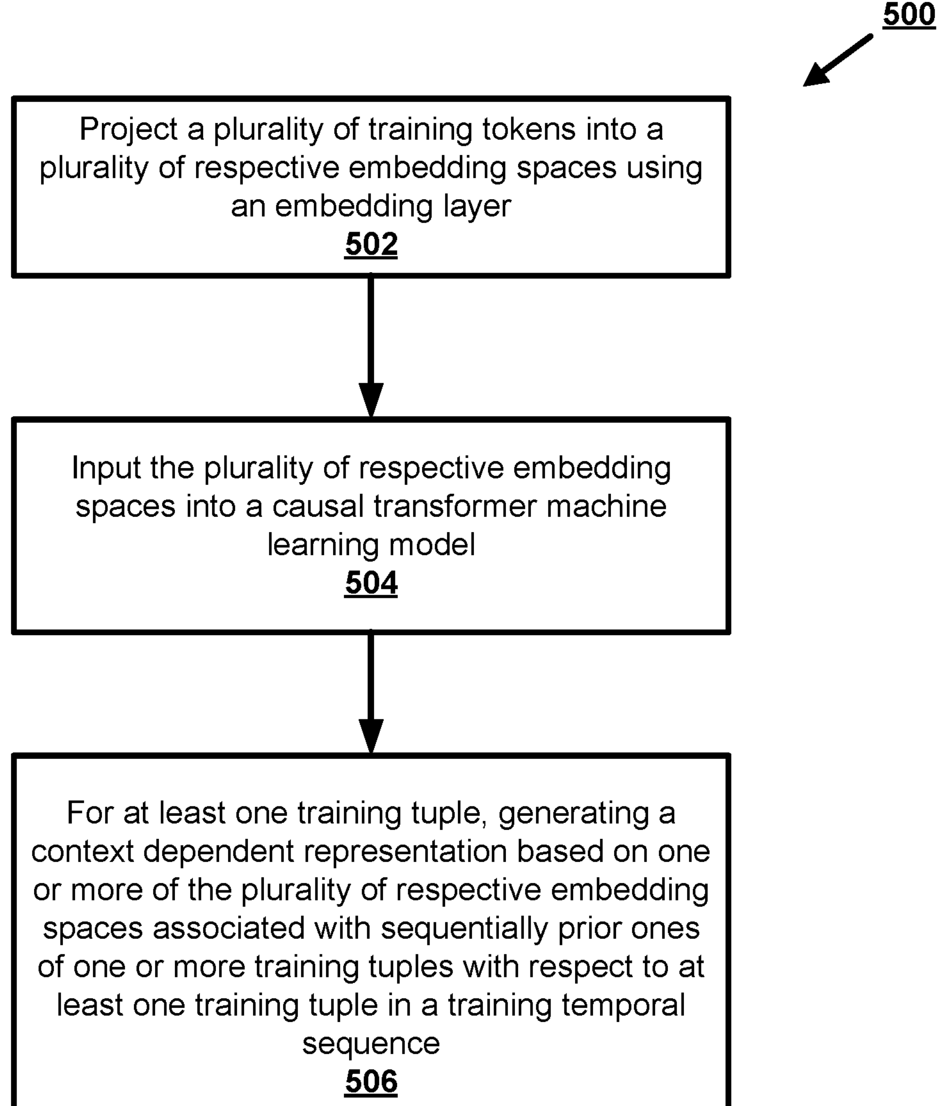
FIG. 5 is a flowchart diagram of an example process for training a causal transformer machine learning model in accordance with some embodiments of the present disclosure.

FIG. 5 is a flowchart diagram of an example process 500 for training a causal transformer machine learning model. In some embodiments, the process 500 begins at step/operation 502 when the predictive data analysis computing entity 106 projects a plurality of training tokens into a plurality of respective embedding spaces using an embedding layer. The plurality of training tokens may be associated with a plurality of training temporal sequences, and at least one of the plurality of training temporal sequences may comprise one or more training tuples.

In some embodiments, a training temporal sequence describes a time series of one or more training tuples associated with instances of training encounters used for training a causal transformer machine learning model. According to some embodiments, a training temporal sequence may comprise a sequence of one or more training tuples, where each training tuple comprises a plurality of training tuple data objects comprising data representative of training states, training combinations of actions, training outcomes, and a training cumulative discounted future outcome.

In some embodiments, a training tuple describes a training encounter instance within a training temporal sequence. A training tuple may comprise a plurality of training tuple data objects. In some embodiments, the one or more training outcomes may be associated with a given one of the one or more training states proceeding a respective one of the one or more training combinations of actions. In some embodiments, the training cumulative discounted future outcome may be associated with a given one of the one or more training tuples within the at least one of plurality of training temporal sequences.

In some embodiments, a training tuple data object describes an attribute of a tuple associated with a training encounter instance within a training temporal sequence. For example, a training tuple of a training temporal sequence may comprise a plurality of training tuple data objects comprising data representative of (i) one or more training states, (ii) one or more training combinations of actions, (iii) one or more training outcomes associated with a given one of the one or more training states proceeding a respective one of the one or more training combinations of actions, and (iv) a training cumulative discounted future outcome associated with the training tuple within the training temporal sequence.

In some embodiments, the embedding layer may translate the plurality of tokens into a real-valued vector such that dense representations of the plurality of tokens are learned in such a way that tokens associated with training tuples co-occurring within a certain window length are closer in vector space than those that are not. The embedding layer may include the following parameters: (a) maximum temporal sequence length, (b) vocabulary size or set of all tokens being embedded, (e.g., for combination of actions tokens—a number of action tokens being considered), and (c) a free tuning parameter for the dimensionality of the vector space. In some embodiments, during training, the training cumulative discounted future outcome may be masked to prevent leakage of information from the future while learning to predict an output combination of actions $$\{a_{t'}\}_{t'=t+1}^{T}$$

or an output state $$\{S_{t'}\}_{t'=t+1}^{T}.$$

In some embodiments, at least one sequentially first ones of the one or more training tuples may be discarded from one or more of the plurality of training temporal sequences to randomize first encounters observed by the causal transformer machine learning model. Discarding training tuples from training temporal sequences may improve training and prediction performance due to the variable length nature of temporal sequences. For example, all temporal sequences may comprise a first tuple but not all of the temporal sequence may comprise a fifth tuple. By discarding selected training tuples, assignments of first tuples within a plurality of temporal sequences may be randomized to mitigate training on a disproportionate amount of data for the earlier tuples in a sequence.

At least one of the plurality of respective embedding spaces may comprise a plurality of embedding sets associated with the plurality of training tokens. In some embodiments, the plurality of embedding sets comprises a temporal embedding set, a structural embedding set, and a positional embedding set.

In some embodiments, a temporal embedding set describes one or more embeddings associated with a relative time between one of a plurality of training tuple data objects and a sequentially first one of the plurality of training tuple data objects in one of a plurality of training temporal sequences.

In some embodiments, a structural embedding set describes one or more embeddings associated with a plurality of respective tuple data object types of a plurality of training tuple data objects.

In some embodiments, a positional embedding set describes one or more embeddings associated with a sequential position of one of a plurality of training tuple data objects in one of a plurality of training temporal sequences.

In some embodiments, at step/operation 504, the predictive data analysis computing entity 106 inputs the plurality of respective embedding spaces into the causal transformer machine learning model.

In some embodiments, at step/operation 506, the predictive data analysis computing entity 106, for at least one of the one or more training tuples, generates a context dependent representation based on one or more of the plurality of respective embedding spaces associated with sequentially prior ones of the one or more training tuples with respect to the at least one training tuple in the training temporal sequence. In some embodiments, a context dependent representation describes an attention mechanism applied in a causal transformer machine learning model for weighting training tuples within a training temporal sequence during training of the causal transformer machine learning model. A causal transformer machine learning model may use a context dependent representation to interpret data from one or more training tuples for generating a prediction output.

In some embodiments, actions selected by the disclosed decision support machine learning model framework may be evaluated on its expected outcome. For example, an estimation of what would have happened had a recommended action been performed may be generated. Additionally, the disclosed decision support machine learning model framework ay be evaluated based on its ability to perform expected outcome estimation and action prediction.

As an example, cumulative discounted future outcome predictions generated by a causal transformer machine learning model of the disclosed decision support machine learning model framework may be evaluated. Based on cumulative discounted future outcomes predicted for each tuple, a causal transformer machine learning model's ability to predict the future may be evaluated. This may be based on an understanding that a good recommendation may rely on the ability to predict future outcomes and should therefore be evaluated on its ability to do so.

As another example, a technique, such as weighted importance sampling may be used to evaluate the disclosed decision support machine learning model framework with respect to average expected outcome (with confidence intervals and variance of expected outcome (with confidence intervals). The average expected outcome may comprise a quantity that measures the expected outcome had policy scoring, generated by the disclosed decision support machine learning model framework, been used. The variance of expected outcome may comprise a quantity that measures variance in outcome had policy scoring, generated by the disclosed decision support machine learning model framework, been used. The variance of expected outcome may be important because it provides a measurement of safety by making sure that policy scoring, generated by the disclosed decision support machine learning model framework, would not result in extreme outcomes that are hidden when measuring only an average.

Accordingly, as described above, various embodiments of the present disclosure make important technical contributions to improving predictive accuracy of causal transformer machine learning models by using a combination of temporal, structural, and positional embeddings to characterize temporal sequences comprising one or more tuples representative of one or more respective encounter instances. This approach improves training speed and training efficiency of training causal transformer machine learning models. It is well-understood in the relevant art that there is typically a tradeoff between predictive accuracy and training speed, such that it is trivial to improve training speed by reducing predictive accuracy. Thus, the challenge is to improve training speed without sacrificing predictive accuracy through innovative model architectures. Accordingly, techniques that improve predictive accuracy without harming training speed, such as the techniques described herein, enable improving training speed given a constant predictive accuracy. In doing so, the techniques described herein improve efficiency and speed of training causal transformer machine learning models, thus reducing the number of computational operations needed and/or the amount of training data entries needed to train causal transformer machine learning models. Accordingly, the techniques described herein improve the computational efficiency, storage-wise efficiency, and/or speed of training machine learning models.

VI. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

VII. Examples

Example 1. A computer-implemented method comprising: receiving, by one or more processors, an input temporal sequence, the input temporal sequence comprising one or more input tuples, at least one of the one or more input tuples comprising a plurality of tuple data objects comprising data representative of (a) one or more states, (b) one or more combinations of actions, (c) one or more outcomes, and (d) a cumulative discounted future outcome associated with the at least one of the one or more input tuples within the input temporal sequence; generating, by the one or more processors, a plurality of input tokens associated with the plurality of tuple data objects, the plurality of tokens generated according to a plurality of respective tuple data object types associated with the plurality of tuple data objects; generating, by the one or more processors and using a causal transformer machine learning model, a prediction output based on the plurality of input tokens and a conditional distribution of actions, the prediction output comprising a plurality of output tokens, wherein training the causal transformer machine learning model comprises: (a) projecting a plurality of training tokens into a plurality of respective embedding spaces using an embedding layer, wherein (i) at least one of the plurality of respective embedding spaces comprises a plurality of embedding sets associated with the plurality of training tokens, (ii) the plurality of embedding sets comprises a temporal embedding set, a structural embedding set, and a positional embedding set, (iii) the plurality of training tokens is associated with a plurality of training temporal sequences, and (iv) at least one of the plurality of training temporal sequences comprises one or more training tuples, wherein at least one of the one or more training tuples comprises a plurality of training tuple data objects comprising data representative of one or more training states, one or more training combinations of actions, one or more training outcomes, and a training cumulative discounted future outcome associated with the at least one of the one or more training tuples within the at least one of plurality of training temporal sequences, (b) inputting the plurality of respective embedding spaces into the causal transformer machine learning model, and (c) for at least one of the one or more training tuples, generating a context dependent representation based on one or more of the plurality of respective embedding spaces associated with sequentially prior ones of the one or more training tuples with respect to the at least one training tuple in the training temporal sequence, and generating, by the one or more processors, one or more policy scores based on the prediction output; and initiating, by the one or more processors, the performance of one or more prediction-based actions based on the one or more policy scores and the prediction output.

Example 2. The computer-implemented method of any of the preceding examples wherein the temporal embedding set comprises one or more embeddings associated with a relative time between one of the one or more training tuples and a sequentially first one of the one or more training tuples in one of the plurality of training temporal sequences.

Example 3. The computer-implemented method of any of the preceding examples wherein the structural embedding set comprises one or more embeddings associated with the plurality of respective tuple data object types of the plurality of training tuple data objects.

Example 4. The computer-implemented method of any of the preceding examples wherein the positional embedding set comprises one or more embeddings associated with a sequential position of one of the one or more training tuples in one of the plurality of training temporal sequences.

Example 5. The computer-implemented method of any of the preceding examples further comprising discarding at least one sequentially first ones of the one or more training tuples from one or more of the plurality of training temporal sequences.

Example 6. The computer-implemented method of any of the preceding examples wherein the causal transformer machine learning model is trained based on teacher-forcing training by using one or more ground-truth tokens as training feedback input to the causal transformer machine learning model.

Example 7. The computer-implemented method of any of the preceding examples wherein the plurality of output tokens comprises one or more output state tokens, one or more output action tokens, one or more output outcome tokens, and one or more output cumulative discounted future outcome tokens.

Example 8. The computer-implemented method of any of the preceding examples wherein generating the prediction output further comprises generating one or more log-likelihood scores of one or more output actions associated with the one or more output action tokens, the log-likelihood scores representative of a likelihood of the one or more output actions most likely to follow based on the input temporal sequence.

Example 9. The computer-implemented method of any of the preceding examples wherein generating the prediction output further comprises generating one or more predictive scores, the one or more predictive scores comprising (i) one or more action predictive scores of one or more output actions associated with the one or more output action tokens based on the one or more states, and (ii) one or more outcome predictive scores associated with one or more output cumulative discounted future outcomes associated with the one or more output cumulative discounted future outcome tokens based on the one or more output actions.

Example 10. The computer-implemented method of any of the preceding examples wherein generating the prediction output further comprises generating one or more expected predicted outcomes based on the one or more output cumulative discounted future outcomes and the one or more predictive scores.

Example 11. The computer-implemented method of any of the preceding examples wherein initiating the performance of the one or more prediction-based action further comprises selecting one or more output actions associated with the one or more output action tokens based on the policy score.

Example 12. The computer-implemented method of any of the preceding examples further comprising excluding one or more of the plurality of action combination tokens from the conditional distribution of actions based on the excluding one or more action combination tokens including probability scores below a threshold.

Example 13. The computer-implemented method of any of the preceding examples wherein generating the plurality of input tokens further comprises: receiving an action space data object comprising a plurality of possible individual actions; and assigning a plurality of action combination tokens to a plurality of combinations comprising selected ones of the plurality of possible individual actions.

Example 14. The computer-implemented method of any of the preceding examples further comprising generating the conditional distribution of actions based on the one or more states.

Example 15. A computing apparatus comprising memory and one or more processors communicatively coupled to the memory, the one or more processors configured to: receive an input temporal sequence, the input temporal sequence comprising one or more input tuples, at least one of the one or more input tuples comprising a plurality of tuple data objects comprising data representative of (a) one or more states, (b) one or more combinations of actions, (c) one or more outcomes, and (d) a cumulative discounted future outcome associated with the at least one of the one or more input tuples within the input temporal sequence; generate a plurality of input tokens associated with the plurality of tuple data objects, the plurality of tokens generated according to a plurality of respective tuple data object types associated with the plurality of tuple data objects; generate, using a causal transformer machine learning model, a prediction output based on the plurality of input tokens and a conditional distribution of actions, the prediction output comprising a plurality of output tokens, wherein training the causal transformer machine learning model comprises: (a) projecting a plurality of training tokens into a plurality of respective embedding spaces using an embedding layer, wherein (i) at least one of the plurality of respective embedding spaces comprises a plurality of embedding sets associated with the plurality of training tokens, (ii) the plurality of embedding sets comprises a temporal embedding set, a structural embedding set, and a positional embedding set, (iii) the plurality of training tokens is associated with a plurality of training temporal sequences, and (iv) at least one of the plurality of training temporal sequences comprises one or more training tuples, wherein at least one of the one or more training tuples comprises a plurality of training tuple data objects comprising data representative of one or more training states, one or more training combinations of actions, one or more training outcomes, and a training cumulative discounted future outcome associated with the at least one of the one or more training tuples within the at least one of plurality of training temporal sequences, (b) inputting the plurality of respective embedding spaces into the causal transformer machine learning model, and (c) for at least one of the one or more training tuples, generating a context dependent representation based on one or more of the plurality of respective embedding spaces associated with sequentially prior ones of the one or more training tuples with respect to the at least one training tuple in the training temporal sequence; generate one or more policy scores based on the prediction output; and initiate the performance of one or more prediction-based actions based on the one or more policy scores and the prediction output.

Example 16. The computing apparatus of any of the preceding examples wherein the temporal embedding set comprises one or more embeddings associated with a relative time between one of the one or more training tuples and a sequentially first one of the one or more training tuples in one of the plurality of training temporal sequences.

Example 17. The computing apparatus of any of the preceding examples wherein the structural embedding set comprises one or more embeddings associated with the plurality of respective tuple data object types of the plurality of training tuple data objects.

Example 18. The computing apparatus of any of the preceding examples wherein the positional embedding set comprises one or more embeddings associated with a sequential position of one of the one or more training tuples in one of the plurality of training temporal sequences.

Example 19. The computing apparatus of any of the preceding examples wherein the one or more processors are further configured to discard at least one sequentially first ones of the one or more training tuples from one or more of the plurality of training temporal sequences.

Example 20. The computing apparatus of any of the preceding examples wherein the causal transformer machine learning model is trained based on teacher-forcing training by using one or more ground-truth tokens as training feedback input to the causal transformer machine learning model.

Example 21. The computing apparatus of any of the preceding examples wherein the plurality of output tokens comprises one or more output state tokens, one or more output action tokens, one or more output outcome tokens, and one or more output cumulative discounted future outcome tokens.

Example 22. The computing apparatus of any of the preceding examples wherein the one or more processors are further configured to generate one or more log-likelihood scores of one or more output actions associated with the one or more output action tokens, the log-likelihood scores representative of a likelihood of the one or more output actions most likely to follow based on the input temporal sequence.

Example 23. The computing apparatus of any of the preceding examples wherein the one or more processors are further configured to generate one or more predictive scores, the one or more predictive scores comprising (i) one or more action predictive scores of one or more output actions associated with the one or more output action tokens based on the one or more states, and (ii) one or more outcome predictive scores associated with one or more output cumulative discounted future outcomes associated with the one or more output cumulative discounted future outcome tokens based on the one or more output actions.

Example 24. The computing apparatus of any of the preceding examples wherein the one or more processors are further configured to generate one or more expected predicted outcomes based on the one or more output cumulative discounted future outcomes and the one or more predictive scores.

Example 25. The computing apparatus of any of the preceding examples wherein the one or more processors are further configured to select one or more output actions associated with the one or more output action tokens based on the policy score.

Example 26. The computing apparatus of any of the preceding examples wherein the one or more processors are further configured to exclude one or more of the plurality of action combination tokens from the conditional distribution of actions based on the excluding one or more action combination tokens including probability scores below a threshold.

Example 27. The computing apparatus of any of the preceding examples wherein the one or more processors are further configured to receive an action space data object comprising a plurality of possible individual actions; and assigning a plurality of action combination tokens to a plurality of combinations comprising selected ones of the plurality of possible individual actions.

Example 28. The computing apparatus of any of the preceding examples wherein the one or more processors are further configured to generate the conditional distribution of actions based on the one or more states.

Example 29. One or more non-transitory computer-readable storage media including instructions that, when executed by one or more processors, cause the one or more processors to: receive an input temporal sequence, the input temporal sequence comprising one or more input tuples, at least one of the one or more input tuples comprising a plurality of tuple data objects comprising data representative of (a) one or more states, (b) one or more combinations of actions, (c) one or more outcomes, and (d) a cumulative discounted future outcome associated with the at least one of the one or more input tuples within the input temporal sequence; generate a plurality of input tokens associated with the plurality of tuple data objects, the plurality of tokens generated according to a plurality of respective tuple data object types associated with the plurality of tuple data objects; generate, using a causal transformer machine learning model, a prediction output based on the plurality of input tokens and a conditional distribution of actions, the prediction output comprising a plurality of output tokens, wherein training the causal transformer machine learning model comprises: (a) projecting a plurality of training tokens into a plurality of respective embedding spaces using an embedding layer, wherein (i) at least one of the plurality of respective embedding spaces comprises a plurality of embedding sets associated with the plurality of training tokens, (ii) the plurality of embedding sets comprises a temporal embedding set, a structural embedding set, and a positional embedding set, (iii) the plurality of training tokens is associated with a plurality of training temporal sequences, and (iv) at least one of the plurality of training temporal sequences comprises one or more training tuples, wherein at least one of the one or more training tuples comprises a plurality of training tuple data objects comprising data representative of one or more training states, one or more training combinations of actions, one or more training outcomes, and a training cumulative discounted future outcome associated with the at least one of the one or more training tuples within the at least one of plurality of training temporal sequences, (b) inputting the plurality of respective embedding spaces into the causal transformer machine learning model, and (c) for at least one of the one or more training tuples, generating a context dependent representation based on one or more of the plurality of respective embedding spaces associated with sequentially prior ones of the one or more training tuples with respect to the at least one training tuple in the training temporal sequence; generate one or more policy scores based on the prediction output; and initiate the performance of one or more prediction-based actions based on the one or more policy scores and the prediction output.

Example 30. The one or more non-transitory computer-readable storage media of any of the preceding examples wherein the temporal embedding set comprises one or more embeddings associated with a relative time between one of the one or more training tuples and a sequentially first one of the one or more training tuples in one of the plurality of training temporal sequences.

Example 31. The one or more non-transitory computer-readable storage media of any of the preceding examples wherein the structural embedding set comprises one or more embeddings associated with the plurality of respective tuple data object types of the plurality of training tuple data objects.

Example 32. The one or more non-transitory computer-readable storage media of any of the preceding examples wherein the positional embedding set comprises one or more embeddings associated with a sequential position of one of the one or more training tuples in one of the plurality of training temporal sequences.

Example 33. The one or more non-transitory computer-readable storage media of any of the preceding examples further causing the one or more processors to discard at least one sequentially first ones of the one or more training tuples from one or more of the plurality of training temporal sequences.

Example 34. The one or more non-transitory computer-readable storage media of any of the preceding examples wherein the causal transformer machine learning model is trained based on teacher-forcing training by using one or more ground-truth tokens as training feedback input to the causal transformer machine learning model.

Example 35. The one or more non-transitory computer-readable storage media of any of the preceding examples wherein the plurality of output tokens comprises one or more output state tokens, one or more output action tokens, one or more output outcome tokens, and one or more output cumulative discounted future outcome tokens.

Example 36. The one or more non-transitory computer-readable storage media of any of the preceding examples further causing the one or more processors to generate one or more log-likelihood scores of one or more output actions associated with the one or more output action tokens, the log-likelihood scores representative of a likelihood of the one or more output actions most likely to follow based on the input temporal sequence.

Example 37. The one or more non-transitory computer-readable storage media of any of the preceding examples further causing the one or more processors to generate one or more predictive scores, the one or more predictive scores comprising (i) one or more action predictive scores of one or more output actions associated with the one or more output action tokens based on the one or more states, and (ii) one or more outcome predictive scores associated with one or more output cumulative discounted future outcomes associated with the one or more output cumulative discounted future outcome tokens based on the one or more output actions.

Example 38. The one or more non-transitory computer-readable storage media of any of the preceding examples further causing the one or more processors to generate one or more expected predicted outcomes based on the one or more output cumulative discounted future outcomes and the one or more predictive scores.

Example 39. The one or more non-transitory computer-readable storage media of any of the preceding examples further causing the one or more processors to select one or more output actions associated with the one or more output action tokens based on the policy score.

Example 40. The one or more non-transitory computer-readable storage media of any of the preceding examples further causing the one or more processors to exclude one or more of the plurality of action combination tokens from the conditional distribution of actions based on the excluding one or more action combination tokens including probability scores below a threshold.

Example 41. The one or more non-transitory computer-readable storage media of any of the preceding examples further causing the one or more processors to receive an action space data object comprising a plurality of possible individual actions; and assigning a plurality of action combination tokens to a plurality of combinations comprising selected ones of the plurality of possible individual actions.

Example 42. The one or more non-transitory computer-readable storage media of any of the preceding examples further causing the one or more processors to generate the conditional distribution of actions based on the one or more states.

The invention claimed is:

1. A computer-implemented method comprising:

receiving, by one or more processors, an input temporal sequence, wherein:

(i) the input temporal sequence comprises a set of one or more input tuples, (ii) an input tuple of the set of one or more input tuples comprises a plurality of tuple data objects comprising data representative of (a) one or more states, (b) one or more combinations of actions, (c) one or more outcomes, and (d) a cumulative discounted future outcome, and (iii) the cumulative discounted future outcome is associated with the input tuple;

generating, by the one or more processors, a plurality of input tokens associated with the plurality of tuple data objects, wherein the plurality of input tokens are generated according to a plurality of respective tuple data object types associated with the plurality of tuple data objects;

generating, by the one or more processors and using a causal transformer machine learning model, a prediction output based on the plurality of input tokens and a conditional distribution of actions, the prediction output comprising a plurality of output tokens, wherein training the causal transformer machine learning model comprises:

(a) projecting a plurality of training tokens into a plurality of respective embedding spaces using an embedding layer, wherein (i) at least one of the plurality of respective embedding spaces comprises a plurality of embedding sets associated with the plurality of training tokens, (ii) the plurality of embedding sets comprises a temporal embedding set, a structural embedding set, and a positional embedding set, (iii) the plurality of training tokens is associated with a plurality of training temporal sequences, and (iv) a training temporal sequence of the plurality of training temporal sequences comprises a set of one or more training tuples, wherein a training tuple of the set of one or more training tuples comprises a plurality of training tuple data objects comprising data representative of one or more training states, one or more training combinations of actions, one or more training outcomes, and a training cumulative discounted future outcome associated with the training tuple, (b) inputting the plurality of respective embedding spaces into the causal transformer machine learning model, and (c) for the training tuple, generating a context dependent representation based on one or more of the plurality of respective embedding spaces associated with one or more sequentially prior tuples of the set of one or more training tuples with respect to the training tuple;

generating, by the one or more processors, one or more policy scores based on the prediction output; and initiating, by the one or more processors, the performance of one or more prediction-based actions based on the one or more policy scores and the prediction output.

2. The computer-implemented method of claim 1, wherein the temporal embedding set comprises one or more embeddings associated with a relative time between the training tuple and a sequentially first training tuple of the set of one or more training tuples.

3. The computer-implemented method of claim 1, wherein the structural embedding set comprises one or more embeddings associated with the plurality of respective tuple data object types of the plurality of training tuple data objects.

4. The computer-implemented method of claim 1, wherein the positional embedding set comprises one or more embeddings associated with a sequential position of the training tuple.

5. The computer-implemented method of claim 1 further comprising discarding at least one sequentially first training tuple of the set of one or more training tuples from a subset of training temporal sequences of the plurality of training temporal sequences.

6. The computer-implemented method of claim 1, wherein the causal transformer machine learning model is trained based on teacher-forcing training by using one or more ground-truth tokens as training feedback input to the causal transformer machine learning model.

7. The computer-implemented method of claim 1, wherein the plurality of output tokens comprises one or more output state tokens, one or more output action tokens, one or more output outcome tokens, and one or more output cumulative discounted future outcome tokens.

8. The computer-implemented method of claim 7, wherein generating the prediction output further comprises generating one or more log- likelihood scores of one or more output actions associated with the one or more output action tokens, the one or more log-likelihood scores representative of a likelihood of the one or more output actions most likely to follow based on the input temporal sequence.

9. The computer-implemented method of claim 7, wherein generating the prediction output further comprises generating one or more predictive scores, the one or more predictive scores comprising (i) one or more action predictive scores of one or more output actions associated with the one or more output action tokens based on the one or more states, and (ii) one or more outcome predictive scores associated with one or more output cumulative discounted future outcomes associated with the one or more output cumulative discounted future outcome tokens based on the one or more output actions.

10. The computer-implemented method of claim 9, wherein generating the prediction output further comprises generating one or more expected predicted outcomes based on the one or more output cumulative discounted future outcomes and the one or more predictive scores.

11. The computer-implemented method of claim 7, wherein initiating the performance of the one or more prediction-based actions further comprises selecting one or more output actions associated with the one or more output action tokens based on the one or more policy scores.

12. The computer-implemented method of claim 1, further comprising excluding one or more action combination tokens of a plurality of action combination tokens from the conditional distribution of actions based on the one or more action combination tokens comprising one or more probability scores that are below a threshold.

13. The computer-implemented method of claim 1, wherein generating the plurality of input tokens further comprises:

receiving an action space data object comprising a plurality of possible individual actions; and assigning a plurality of action combination tokens to a plurality of combinations comprising selected ones a subset of possible individual actions of the plurality of possible individual actions.

14. The computer-implemented method of claim 1 further comprising generating the conditional distribution of actions based on the one or more states.

15. A system comprising one or more processors and one or more non-transitory computer readable media storing processor-executable instructions that, when executed by the one or more processors, cause the one or more processors to perform operations comprising:

receiving an input temporal sequence, wherein:

(i) the input temporal sequence comprises a set of one or more input tuples, (ii) an input tuple of the set of one or more input tuples comprises a plurality of tuple data objects comprising data representative of (a) one or more states, (b) one or more combinations of actions, (c) one or more outcomes, and (d) a cumulative discounted future outcome, and (iii) the cumulative discounted future outcome is associated with the input tuple;

generating a plurality of input tokens associated with the plurality of tuple data objects, wherein the plurality of input tokens are generated according to a plurality of respective tuple data object types associated with the plurality of tuple data objects;

generating, using a causal transformer machine learning model, a prediction output based on the plurality of input tokens and a conditional distribution of actions, the prediction output comprising a plurality of output tokens, wherein training the causal transformer machine learning model comprises:

(a) projecting a plurality of training tokens into a plurality of respective embedding spaces using an embedding layer, wherein (i) at least one of the plurality of respective embedding spaces comprises a plurality of embedding sets associated with the plurality of training tokens, (ii) the plurality of embedding sets comprises a temporal embedding set, a structural embedding set, and a positional embedding set, (iii) the plurality of training tokens is associated with a plurality of training temporal sequences, and (iv) a training temporal sequence of the plurality of training temporal sequences comprises a set of one or more training tuples, wherein a training tuple of the set of one or more training tuples comprises a plurality of training tuple data objects comprising data representative of one or more training states, one or more training combinations of actions, one or more training outcomes, and a training cumulative discounted future outcome associated with the training tuple, (b) inputting the plurality of respective embedding spaces into the causal transformer machine learning model, and (c) for the training tuple, generating a context dependent representation based on one or more of the plurality of respective embedding spaces associated with one or more sequentially prior tuples of the set of one or more training tuples with respect to the training tuple;

generating one or more policy scores based on the prediction output; and initiating the performance of one or more prediction-based actions based on the one or more policy scores and the prediction output.

16. The system of claim 15, wherein the plurality of output tokens comprises one or more output state tokens, one or more output action tokens, one or more output outcome tokens, and one or more output cumulative discounted future outcome tokens.

17. The system of claim 16, wherein the operations further comprise generating the prediction output by generating one or more log-likelihood scores of one or more output actions associated with the one or more output action tokens, the one or more log-likelihood scores representative of a likelihood of the one or more output actions most likely to follow based on the input temporal sequence.

18. The system of claim 16, wherein the operations further comprise generating the prediction output by generating one or more predictive scores, the one or more predictive scores comprising (i) one or more action predictive scores of one or more output actions associated with the one or more output action tokens based on the one or more states, and (ii) one or more outcome predictive scores associated with one or more output cumulative discounted future outcomes associated with the one or more output cumulative discounted future outcome tokens based on the one or more output actions.

19. The system of claim 18, wherein the operations further comprise generating the prediction output by generating one or more expected predicted outcomes based on the one or more output cumulative discounted future outcomes and the one or more predictive scores.

20. One or more non-transitory computer-readable storage media storing instructions that, when executed by one or more processors, cause the one or more processors to perform operations comprising:

receiving an input temporal sequence, wherein:

(i) the input temporal sequence comprises a set of one or more input tuples, (ii) an input tuple of the set of one or more input tuples comprises a plurality of tuple data objects comprising data representative of (a) one or more states, (b) one or more combinations of actions, (c) one or more outcomes, and (d) a cumulative discounted future outcome, and (iii) the cumulative discounted future outcome is associated with the input tuple;

generating a plurality of input tokens associated with the plurality of tuple data objects, wherein the plurality of input tokens are generated according to a plurality of respective tuple data object types associated with the plurality of tuple data objects;

generating, using a causal transformer machine learning model, a prediction output based on the plurality of input tokens and a conditional distribution of actions, the prediction output comprising a plurality of output tokens, wherein training the causal transformer machine learning model comprises:

(a) projecting a plurality of training tokens into a plurality of respective embedding spaces using an embedding layer, wherein (i) at least one of the plurality of respective embedding spaces comprises a plurality of embedding sets associated with the plurality of training tokens, (ii) the plurality of embedding sets comprises a temporal embedding set, a structural embedding set, and a positional embedding set, (iii) the plurality of training tokens is associated with a plurality of training temporal sequences, and (iv) a training temporal sequence of the plurality of training temporal sequences comprises a set of one or more training tuples, wherein a training tuple of the set of one or more training tuples comprises a plurality of training tuple data objects comprising data representative of one or more training states, one or more training combinations of actions, one or more training outcomes, and a training cumulative discounted future outcome associated with training tuple, (b) inputting the plurality of respective embedding spaces into the causal transformer machine learning model, and (c) for the training tuple, generating a context dependent representation based on one or more of the plurality of respective embedding spaces associated with one or more sequentially prior tuples of the set of one or more training tuples with respect to the training tuple;

generating one or more policy scores based on the prediction output; and initiating the performance of one or more prediction-based actions based on the one or more policy scores and the prediction output.

* * * * *